United States Patent [19]

Nagata et al.

[11] Patent Number: 5,225,348
[45] Date of Patent: Jul. 6, 1993

[54] DNA FRAGMENT AND EXPRESSION PLASMID CONTAINING THE DNA FRAGMENT

[75] Inventors: Shigekazu Nagata, Suita; Sumio Sugano, Tokyo; Dong W. Kim, Tokyo; Taichi Uetsuki, Tokyo; Yoshito Kaziro, Tokyo, all of Japan

[73] Assignee: Mochida Pharmaceutical Co., Ltd., Tokyo, Japan

[21] Appl. No.: 447,823

[22] Filed: Dec. 8, 1989

[30] Foreign Application Priority Data

Mar. 14, 1989 [JP] Japan .................................. 1-61702

[51] Int. Cl.⁵ ...................... C12N 15/63; C12N 15/12; C07H 21/04
[52] U.S. Cl. ................................ 435/320.1; 536/24.1; 435/69.1; 435/172.3
[58] Field of Search ................ 435/320.1, 69.1; 935/36, 22, 41; 536/27

[56] References Cited

PUBLICATIONS

Mizushima and Nagata, *Nucleic Acids Research* 18: 5322 (1990).
Uetsuki, et al. Isolation and Characterization of the Human Chromosomal Gene for Polypeptide Chain Elongation Factor-1α*; J. Biol. Chemistry vol. 264, No. 10, pp. 5791-5798 Apr. 5, 1989.

*Primary Examiner*—David L. Lacey
*Assistant Examiner*—George C. Elliott
*Attorney, Agent, or Firm*—Burns, Doane, Swecker & Mathis

[57] ABSTRACT

A DNA fragment containing a promoter region for human polypeptide chain elongation factor-1α, its base sequence and expression plasmids containing the DNA fragment having high applicability to a wide range of host cells with high expression capacity. These expression plasmids can be maintained stably for at least one month in mammalian host cells. Such features of the expression plasmids may render possible the efficient production of various kinds of useful physiologically active substances for a long period using wide range of mammalian cells as the host.

14 Claims, 17 Drawing Sheets

Fig. 1-1

```
1                                                              60                  Met Gly Lys Glu Lys
TTTTCGCAACGGGTTGCCCCCAGAACACAGGTGTCGTGAAAACTACCCCTAAAGCCAA     ATG GGA AAG GAA AAG
                                                                                80
                                                               Cys Gly Ile Asp Lys Arg Thr His Ile Asn Ile
                                                               TGC GGT ATC GAC AAA AGA ACC CAT ATC AAC ATT
          100                                     140
Val Val Ile Gly His Val Asp Ser Gly Lys Ser Thr Thr Gly His Ile Leu Ile Tyr Lys
GTC GTC ATT GGA CAC GTA GAT TCG GGC AAG TCC ACC ACT GGC CAT CTG ATC TAT AAG
                                          160                                     180
                                          Cys Gly Ile Asp Lys Arg Thr Ile Glu
                                          TGC GGT ATC GAC AAA AGA ACC ATT GAA
      200                                     240                                     260
Lys Phe Glu Lys Glu Ala Ala Glu Met Gly Lys Ser Phe Lys Tyr Ala Trp Val Leu Asp Lys Leu Lys Ala Glu Arg Glu Arg Gly
AAA TTT GAG AAG GAG GCT GCT GAG ATG GGA AAG TCC TTC AAG TAT GCC TGG GTC TTG GAT AAA CTG AAA GCT GAG AGA GAG CGT
      280                                     320                                     360
Ile Thr Ile Asp Ile Ser Leu Trp Lys Phe Glu Thr Ser Lys Tyr Tyr Val Thr Ile Ile Asp Ala Pro Gly His Arg Asp Phe Ile Lys
ATC ACC ATT GAT ATC TCC TTG TGG AAA TTT GAG ACA AGC AAG TAC TAT GTG ACT ATC ATT GAT GCC CCA GGA CAC AGA GAC TTT ATC AAA
      380                                     420                                     440
Asn Met Ile Thr Gly Thr Ser Gln Ala Asp Cys Ala Val Leu Ile Val Ala Ala Gly Val Gly Glu Phe Glu Ala Gly Ile Ser Lys Asn
AAC ATG ATT ACA GGG ACA TCT CAG GCT GAC TGT GCT GTC CTG ATT GTT GCT GCT GGT GTT GGT GAA TTT GAA GCT GGT ATC TCC AAG AAT
      460                                     500                                     540
Gly Gln Thr Arg Glu His Ala Leu Leu Ala Tyr Thr Leu Gly Val Lys Gln Leu Ile Val Gly Val Asn Lys Met Asp Ser Thr Glu Pro
GGG CAG ACC CGA GAG CAT GCC CTT CTG GCT TAC ACA CTG GGT GTG AAA CAA CTA ATT GTC GGT GTT AAC AAA ATG GAT TCC ACT GAG CCA
      560                                     600                                     620
Pro Tyr Ser Gln Lys Arg Tyr Glu Glu Ile Val Lys Glu Val Ser Thr Tyr Ile Lys Lys Ile Gly Tyr Asn Pro Asp Thr Val Ala Phe
CCC TAC AGC CAG AAG AGA TAT GAG GAA ATT GTT AAG GAA GTC AGC ACT TAC ATT AAG AAA ATT GGC TAC AAC CCC GAC ACA GTA GCA TTT
      640                                     680                                     720
Val Pro Ile Ser Gly Trp Asn Gly Asp Asn Met Leu Glu Pro Ser Ala Asn Met Pro Trp Phe Lys Gly Trp Lys Val Thr Arg Lys Asp
GTG CCA ATT TCT GGT TGG AAT GGT GAC AAC ATG CTG GAG CCA AGT GCT AAC ATG CCT TGG TTC AAG GGA TGG AAA GTC ACC CGT AAG GAT
      740                                     780                                     800
Gly Asn Ala Ser Gly Thr Thr Leu Leu Glu Ala Leu Asp Cys Ile Leu Pro Pro Thr Arg Pro Thr Asp Lys Pro Leu Arg Leu Pro Leu
GGC AAT GCC AGT GGA ACC ACG CTT GAG GCT CTA GAC TGC ATC CTA CCA CCA ACT CGT CCA ACT GAC AAG CCC TTG CGC CTG CCT CTC
```

Fig. 1-2

```
                820                                   840                                   860                                   880                                   900
Gln Asp Val Tyr Lys Ile Gly Gly Thr Val Pro Val Gly Arg Val Glu Thr Gly Val Leu Lys Pro Gly Met Val Val Thr Phe
CAG GAT GTC TAC AAA ATT GGT GGT ACT GTT CCT GTT GGC CGA GTG GAG ACT GGT GTT CTC AAA CCC GGT ATG GTC GTC ACC TTT 920                                   940                                   960                                   980
Ala Pro Val Asn Val Thr Thr Glu Val Lys Ser Val Glu Met His His Glu Ala Leu Ser Glu Ala Leu Pro Gly Met Asp Asn Gly Phe
GCT CCA GTC AAC GTC ACA ACG GAA GTA AAA TCT GTC GAA ATG CAC CAT GAA GCT CTT CCT GGG GAC AAT GTG GGC TTC 1000                                  1020                                  1040                                  1060                                  1080
Asn Val Lys Asn Val Ser Val Lys Asp Val Arg Arg Gly Asn Val Ala Gly Asp Ser Lys Asn Asp Pro Pro Met Glu Ala Ala Ala Gly Phe
AAT GTC AAG AAT GTG TCT GTC AAG GAT GTT CGT CGT GGC AAC GTT GCT GGT GAC AGC AAA AAT GAC CCA CCA ATG GAA GCA GCT GGC TTC 1100                                  1120                                  1140                                  1160
Thr Ala Gln Val Ile Ile Leu Asn His Pro Gly Gln Ile Ser Ala Gly Tyr Ala Pro Val Leu Asp Cys His Thr Ala His Ile Ala Cys
ACT GCT CAG GTG ATT ATC CTG AAC CAT CCA GGC CAA ATA AGC GCC GGC TAT GCC CCT GTA TTG GAT TGC CAC ACG GCT CAC ATT GCA TGC 1180                                  1200                                  1220                                  1240                                  1260
Lys Phe Ala Glu Leu Lys Glu Lys Ile Asp Arg Arg Ser Gly Lys Lys Leu Glu Asp Gly Pro Lys Phe Leu Lys Ser Gly Asp Ala Ala Ala
AAG TTT GCT GAG CTG AAG GAA AAG ATT GAT CGC CGT TCT GGT AAA AAG CTG GAA GAT GGC CCT AAA TTC TTG AAG TCT GGT GAT GCT GCC 1280                                  1300                                  1320                                  1340
Ile Val Asp Met Pro Gly Lys Pro Met Cys Val Glu Ser Phe Ser Asp Tyr Pro Pro Leu Gly Arg Phe Ala Val Arg Asp Met
ATT GTT GAT ATG CCT GGC AAG CCC ATG TGT GTT GAG AGC TTC TCA GAC TAT CCA CCT TTG GGT CGC TTT GCT GTT CGT GAT ATG 1360                                  1380                                  1400                                  1420
Arg Gln Thr Val Ala Val Gly Val Ile Lys Ala Val Asp Lys Lys Ala Ala Gly Ala Gly Lys Val Thr Lys Ser Ala Gln Lys Ala Gln
AGA CAG ACA GTT GCG GTT GGT GTC ATC AAA GCA GTG GAC AAG AAG GCT GCT GGA GCT GGC AAG GTC ACC AAG TCT GCC CAG AAA GCT CAG

Lys Ala Lys End        1460                          1480                                  1500                                  1520                                  1540
AAG GCT AAA TGA ATATTATCCCTAATACCTGCCACCCCACTCTTAATCAGTGGTGGAAGAACGGTCTCAGAACTGTTGTTTGTTCAATTGGCCATTTAAGTTTAGTTAGTAAAAGACT 1560                          1580                                  1600                                  1620                                  1640                                  1660
GGTTAATGATAACATGCATCGTAAAACCTTCAGAAGGAAAGGAGAATGTTTGTGGACCACTTGTTTCTTTTTGCGTGTGGCAGTTTAAGTTATTAGTTTTTAAAATCAGTAC 1680                          1700                                  1720                                  1740
TTTTTAA TGGAAACAACTTGACCAAAAATTTGTCACAGAATTTTGAGACCCATTAAAAAAGTTAAATGAGAAAAAAAAA
```

Fig. 3-1

```
                        20                      40                      60                      80                     100
          CCCGGGGCTGGGCTGAGACCCCAGAGAGAAGACGCCTGAGGATTTGTCCCGGACTACCGAGATGCCAAGGCTGAGGACGGAGGCTGATTGAGAGGGAAGGCTACACCCTAATCTCAAT
                        120                     140                     160                     180                     200
          ACAACCTTTGAGCTAAGCAGCAATGTAGAGGGAAGATTCTGCACGTCCCTTCCAGGGCCCTCCACCACCCCCCAACCCGGCCCGCACCGGAGCTGAGTAATTCATAC
                        220                     240                     260                     280                     300
          AAAAGGACTCGCCCTGCCTTGGGGAATCCCAGGGACCGTCGTTAAACTCCCACTAACGTAGAACCCAGAGATCGCTGCGTTCCCCGCCCCTCTCGTCATCACTGAG
                        320                     340                     360                     380                     400
          GTGGAGAAGAGCATGCCTGAGGCTCCGTCGCCCAGTGGGCAGAGCCACATCGGGGAGAAGTGGGGGAGGGGTCGGCAATTGAACCGTCCTAGAGAAGGTGG
                        420                     440                     460                     480                     500
          CCGGGGGTAAACTGGGAAAGTGATGTCGTACTGGCTCCCGCCTTTCCCGAGGTGGGGGAGAACCGTATATAAGTGCAGTAGTGCCGTGAACGTTCTTTTTCGCAACCGGGTTGC
                  intron 1               540                     560              * exon 1 1              600                     620
          CGCCAGAACACAG  GTAAGTGCGTGTGTGGTTCCCCGGGGCCTGGCCTCTTTACCGGTTATGGCCGTTGAGTTGCCTGAATTACTTCCACGCCCCTGCCAGTACGTGATTCTTGA
                        640                     660                     680                     700                     720
          TCCCGACTTCGGGTGGAAGTGGTGGTGGAGAGTTCGAGGCCTTCAGGCCTCCGCCTCGTCGTTGAGGGCGCTTTTTTCGGCAAGATAGTCTTGTAAATGCGGGGCCAAGAATCT
                        740                     760                     780                     800                     820
          GGTGGCACTCTGTATTTCGGTTTTGGGCGGACCGCCCCGCTGCCGTGCCCCCAGGCGGGTGCCGAGCCGGGGGCCACCGAGAATCGGACGGGGGTA
                        840                     860                     880                     900                     920
          CTGCACACTGGTATTCGGTTTTGGGCGGGACCGCCCCGCTGCCGTGCCCCCAGGCGGGTGCCGAGCCGGGGGCCACCGAGAATCGGACGGGGGTA
                        940                     960                     980                    1000                    1020
          GTCTCAAGCTGGCCCGCCGCTCTGGTCGCTCGGGCCCGCCGCCGTAATCGCCGCCCGCCAAGGCTGGCCCAGTTGCGTGAGCGGAAAGATGGCCGCTTC
                       1040                    1060                    1080                    1100                    1120
          CCGGCCCTGCTCCAGGAGCTCAAAATGGAGGACGCGGGAGAGCGGGGAGTCACCCACAAAGGAAAAAGGGCCTTTCCGTCCTCCAGCCGTCCGTTCATGTGACTCC
                       1140                    1160                    1180                    1200                    1220
          ACGGAGTACCGGGGCCCTCGGCACCCTCAGGCACTTAGTTCTCGAGCTTTTGGAGTACGTCGTCTTTAGGTTGGGGGGAGGGGTTTATGCGATGGAGTTCCCACACTGAGTGGGTGGA
                       1240                    1260                    1280                    1300                    1320
          GACTGAAGTAGGCCAGCTTGGCACTTGATGTAATTCTCCTTGAATTCGCCCTTTTGAGTTTTGGATCTTGGTTCATTCTCAAGCCTCAGACAGTGGTTCAAAGTTTTTTCTTCCAT
          exon 2                           1340                    1360                    1380
          TTCAG  GTGTCGTCGTGAAAACTACCCCAAA  ATG GGA AAG GAA AAG GAA ACT ATC CAT AAG ACT ATC GTC ATT GGA CAC GTA GAT TCG GGC AAG
                                           Met Gly Lys Glu Lys Glu Thr His Lys Thr Ile Val Ile Gly His Val Asp Ser Gly Lys
                                            1                         10                                        20
                       1660                    1680                    1700                                    1720
          TCC ACT ACT GGC CAT CTG ATC TAT AAA TGC GGT GGC ATC GAC AAA AGA ACC ATT GAA AAA TTT GAG AAG GAG GCT GAG GTATGTT
          Ser Thr Thr Gly His Leu Ile Tyr Lys Cys Gly Gly Ile Asp Lys Arg Thr Ile Glu Lys Phe Glu Lys Glu Ala Glu
                                    30                                    40
```

Fig. 3-2

```
intron 2      1760              1780              1800              1820              1840
TAATACCAGAAAGGGAAAGATCAACTAAAATGAGTTTTACCACCAGAATCATTAGTGATTCCCCAGAACTAGTGAGTTGTTAGATCTGAATGCTAATAGTTAAGACCTTACTATG
   1860              1880              1900              1920              1940              1960
AAATAATTTGCTTTGGTGACTTCGTAATCGTATCGTAGTAGATTGAGTGAGATTTAAGATCTACTTATAAAAGTTGATTTGATTTTGGTTGCTTCTGTAACCCAAGTG
   1980              2000              2020              2040              2060              2080
ACCAAAATCACTTGGACTTGGAGTTGTAAAGTGGAAACTGCCAATTAAGGGCTGGGGACAAGGAAATTGAAGCTGGAGTTGTGTTGTTTAGTAACCAAGTAACGACTCTAATCTTAC
exon 3                                                          2140                            2180
AG ATG GGA AAG GGC TCC TTC AAG TAT GCC TGG GTC TTG GAT AAA CTG GAA GCT GTT GAA CGT GAA GGT ATC ACC ATT GAT ATC TCC TTG
   Met Gly Lys Gly Ser Phe Lys Tyr Ala Trp Val Leu Asp Lys Leu Ala Lys Val Glu Arg Glu Gly Ile Thr Ile Asp Ile Ser Leu
                                 50                                60                                70

2200                            2240                            2260
TGG AAA TTT GAG ACC AGC AAG TAC TAT GTG ACT ATC ATT GAT GCC CCA GGA CAC AGA GAC TTT ATC AAA AAC ATG ATT ACA GGG ACA TCT
Trp Lys Phe Glu Thr Ser Lys Tyr Tyr Val Thr Ile Ile Asp Ala Pro Gly His Arg Asp Phe Ile Lys Asn Met Ile Thr Gly Thr Ser
                                 80                                90                               100
                                                                                                                   2380
intron 3          2300                            2340                            2360                     GCT GAC
CAG GTTGGGATTAATAATTCTAGGTTTCTTATCCCAAAGGCTTGCTTTGTCACTGGTTTGTCATTGGAGTTGACAGGGATATGCTTGCTTCTTTAAAG Ala Asp
Gln                                                                                                            110
exon 4              2400                            2440                            2460                            
TGT GCT GTC CTG ATT GTT GCT GGT GTT GAA GCT GGT ATC TCC GGT GAA AAT GGG CAG ACC CGA GAG CAT GCC CTT CTG GCT
Cys Ala Val Leu Ile Val Ala Gly Val Glu Ala Gly Ile Ser Gly Glu Asn Gly Gln Thr Arg Glu His Ala Leu Leu Ala
                                120                               130                               140
   2480                            2520                            2540                            2560
TAC ACA CTG GGT GTG AAA CAA CTA ATT GTC GGT GTT AAC AAA ATG GAT TCC ACT GAG CCA CCA TAC AGC CAG AAG AGA TAT GAG GAA ATT
Tyr Thr Leu Gly Val Lys Gln Leu Ile Val Gly Val Asn Lys Met Asp Ser Thr Glu Pro Pro Tyr Ser Gln Lys Arg Tyr Glu Glu Ile
                                150                               160                               170
                      2600                            2620                            2640
GTT AAG GAA GTC AGC ACT TAC ATT AAG AAA ATT GGC TAC GAC ACA GCA TTT GTG CCA ATT TCT GGT TGG AAT GGT GAC AAC
Val Lys Glu Val Ser Thr Tyr Ile Lys Lys Ile Gly Tyr Asp Thr Ala Phe Val Pro Ile Ser Gly Trp Asn Gly Asp Asn
                                180                               190                               200
                                            intron 4                                                        2760
ATG CTG GAG CCA AGT GCT AAC GTAAGTGGCTTTCAAGACCATTGTTAAAAGCTCTGGAATGCCGATTTCATGCTTACACAAATTGGGCATGCTGTGTTTCAG ATG CCT
Met Leu Glu Pro Ser Ala Asn                                                                                    Met Pro
exon 5    2780                            2820                            2840
TGG TTC AAG GGA TGG AAA GTC ACC CGT AAG GAT GGC AAT GCC AGT GGA ACC ACG CTG CTT GAG GCT CTA CCA CCA ACT
Trp Phe Lys Gly Trp Lys Val Thr Arg Lys Asp Gly Asn Ala Ser Gly Thr Thr Leu Leu Glu Ala Leu Asp Cys Ile Leu Pro Pro Thr
210                               220                               230
            2880                            2900         intron 5     2940
CGT CCA ACT GAC AAG CCC CTG CGC CTC CCT CTC CAG GAT GTC TAC AAA ATT GGT G GTAAGTTGGCTGTAAACAAGTTGAATTTGAGTTGATAGAGTACT
Arg Pro Thr Asp Lys Pro Leu Arg Leu Pro Leu Gln Asp Val Tyr Lys Ile Gly G
240                               250
```

Fig. 3-3

```
       2960                                           exon 6           3020                                              3040
GTCTGCCTTCATAGGTATTTAGTATGCTGAAATATTTTAG GT ATT GGT ACT GTT CCT GTT GGC CGA GTG GAG ACT GGT GTC AAA CCC GGT ATG
                                         ly Ile Gly Thr Val Pro Val Gly Arg Val Glu Thr Gly Val Leu Lys Pro Gly Met
                                          260                                              270
      3060                                           3080                                           3100                                           3120                                             3140
GTG GTC ACC TTT GCT CCA GTC AAC GTT ACA ACG GAA GTA AAA TCT GTC GAA ATG CAC CAT GAA GCT TTG AGT GAA GCT CTT CCT GGG GAC
Val Val Thr Phe Ala Pro Val Asn Val Thr Thr Glu Val Lys Ser Val Glu Met His His Glu Ala Leu Ser Glu Ala Leu Pro Gly Asp
                        280                                             290                                              300
                                           3160                                             intron 6              3200                                             3220
AAT GTG GGC TTC AAT GTC AAG AAT GTG TCT CGT CGA AGA AAT GTT GCT GAC AGC AAA AAT GAC CCA AGT AAG AAT GAC CCT CCA ATG GAA
Asn Val Gly Phe Asn Val Lys Asn Val Ser Arg Arg Asn Val Ala Gly Asp Ser Lys Asn Asp Pro Ser Lys Asn Asp Pro Pro Met Glu
                        310                                             320                                              330
     3240                                           exon 7                3280                                             3300                                              3340
GCA GCT GGC TTC ACT GCT CAG GTAACAATTTAAAGTAACATTAACTTATTGCAGAGGCTAAAGTCATTTGAGACTTTGGATTTGCACTGAATGCAAATCTTTTTCCAAG
Ala Ala Gly Phe Thr Ala Gln
                        340
          exon 7           3360                                             3380                                             3400                                             3420
GTG ATT ATC CTG AAC CAT CCA GGC CAA ATA AGC GCC GGC TAT GCC CCT GTA TTG GAT TGC CAC ACG GCT CAC ATT GCA TGC AAG TTT GCT
Val Ile Ile Leu Asn His Pro Gly Gln Ile Ser Ala Gly Tyr Ala Pro Val Leu Asp Cys His Thr Ala His Ile Ala Cys Lys Phe Ala
                        350                                             360                                              370
     3440                                             3460                                             3480                                             3500                                             3520
GAG CTG AAG GAA AAG ATT GAT CGC TCT CGT TCT GGT AAA AAG CTG GAA GAT GGC GGG CCT AAA TTC TTG AAG TCT GGT GAT GCT ATT GTT GAT
Glu Leu Lys Glu Lys Ile Asp Arg Ser Arg Ser Gly Lys Lys Leu Glu Asp Gly Gly Pro Lys Phe Leu Lys Ser Gly Asp Ala Ile Val Asp
                        380                                             390                                              400
     3540                                             3560                                             intron 7         3600                                             3620
ATG GTT CCT GGC AAG CCC ATG TGT GTT GAG AGC TTC TCA GAC TAT CCA CCT TTG G GTAAGGATGACTACTTAAATGTAAAAAAGTGTGTTAAAGATGAA
Met Val Pro Gly Lys Pro Met Cys Val Glu Ser Phe Ser Asp Tyr Pro Pro Leu G
                        410                                             420
     3640                                            3660                                              3700                                             3720
AAATACAACTGAACAGTACTTTGGGTAATAATTAACTTTTTTTTTAATAG GT CGC TTT GCT GTT CGT GAT ATG AGA CAG ACA GTT GCG GTG GTC ATC
                                                    ly Arg Phe Ala Val Arg Asp Met Arg Gln Thr Val Ala Gly Val Ile
                                                                        430
     3740                                             3760                                             3780                                              3800
AAA GCA GTG GAC AAG AAG GCT AAG GCT GGA GCT GTC ACC AAG TCT GCC CAG AAA GCT CAG AAG TCT AAA TGA ATATTATCCCTAATACCTG
Lys Ala Val Asp Lys Lys Ala Lys Ala Gly Ala Val Thr Lys Ser Ala Gln Lys Ala Gln Lys Ser Lys End
                        440                                             450                                              460
     3820                                             3860                                             3880                                              3900                                           3920
CCACCCCACTCTTAATCAGTGGTGGAAGAACGGTCTCAGAACTGTTGTTTCAATGGCCATTTAAGTTTAGTAGTAAAAGACTGGTTAATGATAACAATGCATCGTAAACCTTCAGA
```

Fig. 3-4

```
     3940              3960              3980              4000              4020              4040
AGGAAAGGAGAAATGTTTCTGGACCACTTTGGTTTCTTTTTTGCGTGTGGCAGTTTTAAGTTATTAGTTTTAAAATCAGTACTTTTAATGAACAACTTGACCAAAAATTTGTCA 4060              4080              4100              4120              4140              4160
CAGAATTTGAGACCCATTAAAAAGTAAATGAGAAACCTGTGTGTTCCTTGGTCAACACCGAGACATTTAGGTGAAAGACATCTAATTCTGGTTTACGAATCTGGAAACTTCTTG 4180              4200              4220              4240              4260              4280
AAAATGTAATTCTGAGTTAACACTTCTCGGGTGGAGAATAGGGTTGTTTTCCCCCCACATAATTGGAAGGGGAAGGAATATCATTAAAGCTATGGAGGGTTTCTTTGATTACAACAC 4300              4320              4340              4360              4380              4400
TGGAGAGAAATGCAGCATGTTGCTGATTGCCCTGTCACTAAAACAGGCCAAAACTGAGTCCTTGGGTTGCATAGAAAGCTTCATGTTGCTAAACCAATGTTAAGTGAATCTTTGGAAAC 4420              4440              4460              4480              4500              4520
AAAATGTTCCAAATTACTGGGATGTGCATGTTGAAACGTGGGTTAAATGACTGGGCAGTGAAAGTTGACTATTTGCCATGACTAAGAAATAAGTGTAGTGGCTAGTGTACACCCTA 4540              4560              4580              4600              4620              4640
TGAGTGGAAGGGTCCATTTGAAGTCAGTGGAGTAAGCTTTATGCCATTTGATGGTTTCACAAGTTCTATTGAGTTGCTATTCAGAATAGGAACAAGGTTCTAATAGAAAAGATGCA 4660              4680
ATTTGAAGTAGTCTATAAAATTAGACTAATTACATTGCTTTCTCCGAC
```

— indicates human EF-1α chromosomal gene.

| indicates exons in human EF-1α chromosomal gene. (Exons are numbered consecutively.)

DNA FRAGMENT AND EXPRESSION PLASMID CONTAINING THE DNA FRAGMENT

BACKGROUND OF THE INVENTION

This invention relates to a novel DNA fragment having an active promoter region and some expression plasmids containing said DNA fragment, both of which are effective for use in the production of physiologically active substances by means of recombinant DNA technology. In particular, this invention relates to a novel DNA fragment having the promoter region of a human polypeptide chain elongation factor gene and some expression plasmids containing said DNA fragment.

With the advance of gene engineering studies, production of substances by recombinant DNA technology has come into a common means. Methods have been established almost completely for the production of foreign proteins by means of recombinant DNA technology using *E. coli* as the host. The use of *E. coli*, however, is still inappropriate for the production of a protein which essentially requires the addition of sugar chains or a protein whose physiological activity or antigenicity is altered when it is produced in a different cell type.

For the purpose of solving such a problem, various host systems have been developed using animal cells. In general, three signals are required for the gene expression in animal cells; that is, promoter, RNA splicing signal and poly (A) addition signal. It is important to select efficient promoter for a high level expression of the gene for a protein of interest. Promoters which are being used commonly include the SV40 (a papovavirus) early promoter, adenovirus major late promoter and metallothionein promoter originated from mouse and the like. The SV40 early promoter is being used most frequently, but this promoter still has the disadvantage of low level expression capacity and narrow host range. In other words, tissue-specific expression and cell type-dependent changes in the level of expression capacity are unavoidable even if the SV40 early promoter is used. For example, the expression capacity is remarkably low in lymphoid cells and nerve cells compared to other cell types.

Recently, Y. Takebe et al. (*Mol. Cell. Biol.*, vol. 8, p. 466, 1988) have constructed an SRα promoter by incorporating a portion of the terminal repeat sequence of human T-cell leukemia virus type 1 into downstream of the SV40 early promoter. According to the report, expression of the downstream gene of the SRα promoter was 1 or 2 orders of magnitude more active than that of the SV40 early promoter when a certain lymphoid cell was used as the host. However, it is still unclear whether the SRα promoter can maintain its high expression capacity in other host cells. If the diversity of useful physiologically active substances which will be produced in the future by means of recombinant DNA technology is taken into consideration, it is necessary to obtain a new promoter that has high level of expression capacity in more wider range of host cells and to develop an expression plasmid containing such a promoter.

SUMMARY OF THE INVENTION

Taking the above-described situation of the prior art in consideration, the present inventors have performed studies on the screening of a novel DNA fragment containing a promoter region which could show high expression capacity in wide range of host cells and on the development of an expression plasmid containing said DNA fragment. Through these studies, the present inventors have isolated a chromosomal gene encoding human polypeptide chain elongation factor-1α (to be referred to as human EF-1α hereinafter) which is constitutively produced in all human cells and have revealed structure of said gene by determining its base sequence for the first time.

Some expression plasmids were then constructed using a novel DNA sequence containing a promoter region for said gene. These expression plasmids were found to be applicable efficiently to wider range of host cells with higher expression capacity compared to the commonly used expression plasmids. The present invention has been accomplished as a result of these efforts.

Polypeptide chain elongation factors are enzymes which take parts in the polypeptide chain elongation reaction in the translation process, and classified into two groups in terms of its functions; that is, a factor which the catalytic binding of aminoacyl-tRNA to the A site of a ribosome and the other factor which transfers peptidyl-tRNA from the A site to the P site of a ribosome.

In the case of procaryotic cells, above-described two kinds of polypeptide chain elongation factor (to be referred to as EF hereinafter) are called EF-T and EF-G, respectively, and the EF-T is divided further into EF-Tu and EF-Ts. In eucaryotic organisms, on the other hand, different EFs are located in cytoplasm and mitochondria independently. As a cytoplasmic EF, EF-1α whose function is equivalent to that of EF-Tu in *E. coli* has been found and purified from various cells and tissues of yeast, pig liver and the like.

Primary structure of human EF-1α cDNA has been determined by J. H. G. M. Brands et al. (*Eur. J. Biochem.*, vol. 155, p. 167, 1986). However, DNA sequence of the chromosomal gene has not been revealed, because, as will be described later, isolation of human EF-1α chromosomal gene was difficult to achieve due to the presence of many human EF-1α pseudogenes in the chromosome genes. As described above, the present inventors have isolated a human EF-1α chromosome gene, determined its base sequence and revealed for the first time a novel DNA sequence containing a promoter region of the human EF-1α gene and the DNA sequence of introns. After that, the inventors have found that the novel DNA fragment containing said promoter region stimulated the expression of its downstream gene and have constructed a high expression plasmid containing said DNA fragment.

First aspect of the present invention provides a novel DNA fragment containing a promoter region for a human polypeptide chain elongation factor gene.

The second aspect of the present invention provides an expression plasmid constructed by using a novel DNA fragment containing a promoter region of human polypeptide chain elongation factor gene.

Preferably, the human polypeptide chain elongation factor gene may be the human polypeptide chain elongation factor-1α gene.

The present invention also provides a novel DNA fragment comprising at least a portion or a whole of a region of about 2.5 kilo base pairs which is located immediately upstream of the initiation codon of the human polypeptide chain elongation factor gene.

The novel DNA fragment preferably contains a promoter region for human polypeptide chain elongation factor-1α gene, which is represented by the following sequence (I):

```
C C C G G G C T G G G C T G A G A C C C G C A G A G G A A G A C G C T C T A G G   40
G A T T T G T C C C G G A C T A G C G A G A T G G C A A G G C T G A G G A C G G   80
G A G G C T G A T T G A G A G G C G A A G G T A C A C C C T A A T C T C A A T A   120
C A A C C T T T G G A G C T A A G C C A G C A A T G G T A G A G G G A A G A T T   160
C T G C A C G T C C C T T C C A G G C G G C C T C C C C G T C A C C A C C C C    200
C C C A A C C C G C C C C G A C C G G A G C T G A G A G T A A T T C A T A C A A   240
A A G G A C T C G C C C C T G C C T T G G G G A A T C C C A G G G A C C G T C G   280
T T A A A C T C C C A C T A A C G T A G A A C C C A G A G A T C G C T G C G T T   320
C C C G C C C C C T C A C C C G C C C G C T C T C G T C A T C A C T G A G G T G   360
G A G A A G A G C A T G C G T G A G G C T C C G G T G C C C G T C A G T G G G C   400
A G A G C G C A C A T C G C C C A C A G T C C C C G A G A A G T T G G G G G G A   440
G G G G T C G G C A A T T G A A C C G G T G C C T A G A G A A G G T G G C G C G   480
G G G T A A A C T G G G A A A G T G A T G T C G T G T A C T G G C T C C G C C T   520
T T T T C C C G A G G G T G G G G G A G A A C C G T A T A T A A G T G C A G T A   560
                                         ─────────── ↑
                                              220 ↑

G T C G C C G T G A A C G T T Ċ T T T T T C G C A A C G G G T T T G C C G C C A   600
                              223 ↑                           204 ↑

G A A C A C A G G T A A G T G C C G T G T G T G G T T C C C G C G G G C C T G G   640
C C T C T T T A C G G G T T A T G G C C C T T G C G T G C C T T G A A T T A C T   680
T C C A C G C C C C T G G C T G C A G T A C G T G A T T C T T G A T C C C G A G   720
C T T C G G G T T G G A A G T G G G T G G G A G A G T T C G A G G C C T T G C G   760
C T T A A G G A G C C C C T T C G C C T C G T G C T T G A G T T G A G G C C T G   800
G C C T G G G C G C T G G G G C C G C C G C G T G C G A A T C T G G T G G C A C   840
C T T C G C G C C T G T C T C G C T G C T T T C G A T A A G T C T C T A G C C A   880
T T T A A A A T T T T T G A T G A C C T G C T G C G A C G C T T T T T T T C T G   920
G C A A G A T A G T C T T G T A A A T G C G G G C C A A G A T C T G C A C A C T   960
G G T A T T T C G G T T T T T G G G G C C G C G G G C G G C G A C G G G G C C C   1000
G T G C G T C C C A G C G C A C A T G T T C G G C G A G G C G G G G C C T G C G   1040
A G C G C G G C C A C C G A G A A T C G G A C G G G G G T A G T C T C A A G C T   1080
G G C C G G C C T G C T C T G G T G C C T G G C C T C G C G C C G C C G T G T A   1120
T C G C C C C G C C C T G G G C G G C A A G G C T G G C C C G G T C G G C A C C   1160
A G T T G C G T G A G C G G A A A G A T G G C C G C T T C C C G G C C C T G C T   1200
G C A G G G A G C T C A A A A T G G A G G A C G C G G C G C T C G G G A G A G C   1240
G G G C G G G T G A G T C A C C C A C A C A A A G G A A A A G G G C C T T T C C   1280
G T C C T C A G C C G T C G C T T C A T G T G A C T C C A C G G A G T A C C G G   1320
G C G C C G T C C A G G C A C C T C G A T T A G T T C T C G A G C T T T T G G A   1360
G T A C G T C G T C T T T A G G T T G G G G G G A G G G G T T T T A T G C G A T   1400
G G A G T T T C C C C A C A C T G A G T G G G T G G A G A C T G A A G T T A G G   1440
```

```
-continued
C C A G C T T G G C A C T T G A T G T A A T T C T C C T T G G A A T T T G C C C  1480

T T T T T G A G T T T G G A T C T T G G T T C A T T C T C A A G C C T C A G A C  1520

A G T G G T T C A A A G T T T T T T T C T T C C A T T T C A G G T G T C G T G A  1560

A 1561
↑
↑ 321 . . . (I).
```

Preferably, the novel DNA fragment may contain at least a portion or a whole of the base sequence of the present invention.

It is known commonly that chromosomal DNA sequences, excluding structural gene, vary from one another by slight degrees depending on the host cells, mutation and the like, without altering the main activity. Accordingly, it is intended to include within the scope of the present invention all variations of the novel DNA fragment of the present invention and the novel base sequence represented in sequence (I), wherein the base sequence is slightly modified by artificial mutation and the like, on condition that the function of these variants is the same as that of the DNA of the present invention.

BRIEF DESCRIPTION OF THE DRAWINGS

FIG. 1-1 to 1-2 shows base sequence of human polypeptide chain elongation factor-1α cDNA.

FIG. 2 shows the organization of human polypeptide chain elongation factor-1α chromosomal gene and diagrammatic view of the sequencing strategy including the direction and length of sequence.

FIG. 3-1 to 3-4 shows complete base sequence of human polypeptide chain elongation factor-1α chromosomal gene.

FIG. 4 shows a flow diagram for the construction of plasmids pEF-2 and pEF-3.

FIGS. 11 and 12 show results of the detection of T antigen in IMR-32 cells by means of a fluorescence antibody technique, FIGS. 13 and 14 show results of the detection of T antigen in 3Y1 cells by the same technique and FIG. 15 shows a result of the detection of human CD4 in CHO-K1 cells by the same technique.

DETAILED DESCRIPTION OF THE INVENTION

Figure 2:
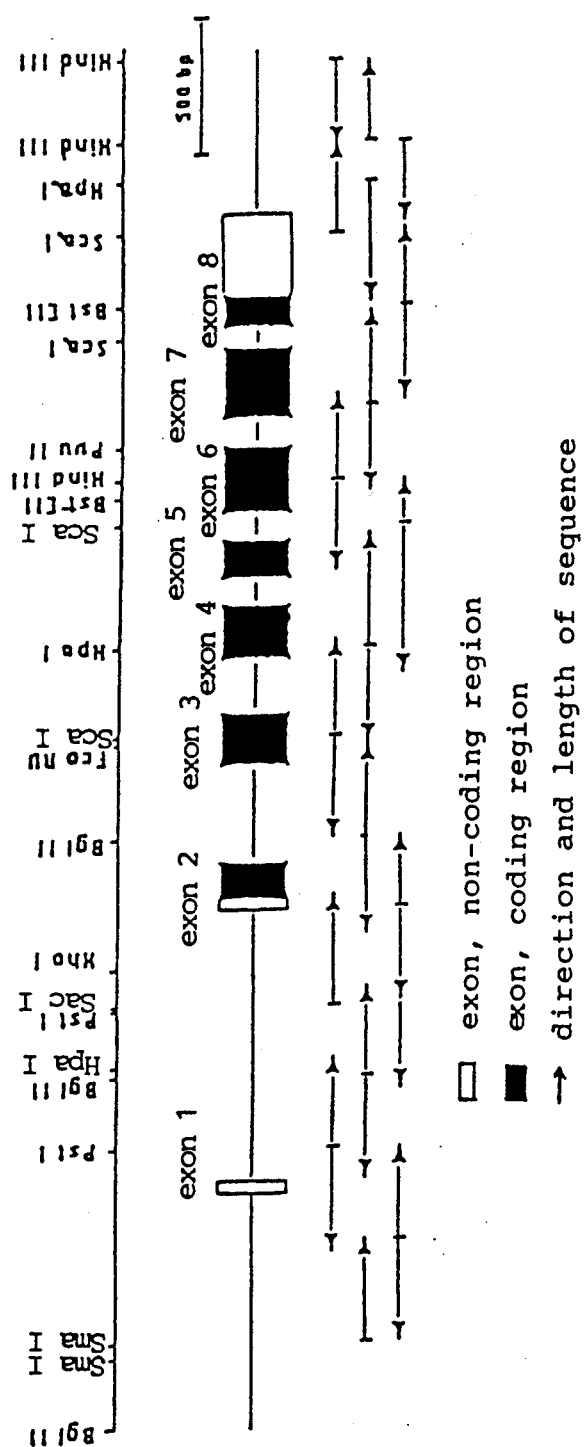

Human EF-1α chromosomal gene may be obtained by means of nucleic acid hybridization from a human gene library using an appropriate probe. The gene library constructed from human fetal liver (R. M. Lawn et al.; Cell, vol. 15, p. 1157, 1978), human placenta (H. Matsushime et al.; Mol. Cell. Biol., vol. 6, p. 3000, 1986) and the like can be used as the human gene library.

Regarding a probe for use in the screening, any DNA or RNA preparation having the base sequence or complementary sequence of human EF-1α may be useful. The DNA or RNA preparation may be obtained from any eucaryotic origin, preferably from human tissues. More preferably, human EF-1α cDNA or an oligonucleotide having complementary base sequence to the cDNA may be used. Radiation labeling of human EF-1α cDNA may be performed using a commercially available nick translation kit and the like. A cDNA or an oligonucleotide having complementary base sequence to the cDNA synthesized using a DNA synthesizer may also be used as a probe by labeling them with [$\gamma$-$^{32}$P]. It is known that human chromosomes are possessed of pseudogenes each of which have the same DNA sequence of a certain gene but which show no function. For the purpose of avoiding cloning of the pseudogene, it is preferable to use a DNA sequence which has no homology between the cDNA and EF-1α pseudogene. A base sequence of the 3' non-coding region of the human EF-1α cDNA is suitable for this purpose.

In this case, it is necessary to confirm the presence of the coding region for the human EF-1α cDNA in the positive clones thus obtained, by means of Southern hybridization and the like using said coding region as the probe. Also, it is necessary to confirm, by determining base sequence of a positive clone, that the positive clone is identical with the EF-1α chromosomal gene, but not a pseudogene which is processed by deletion, insertion or mutation.

The human EF-1α chromosomal gene thus obtained is then subcloned into a commonly used plasmid. Any plasmid may be useful. pUC plasmids are preferable. Restriction enzyme digestion map of a plasmid thus prepared can be obtained by digesting the plasmid with various restriction enzymes. Human EF-1α chromosomal gene is digested into appropriate size of DNA fragments according to the restriction enzyme digestion map, and these DNA fragments are subcloned into phage vector M13 mp8 or M13 mp9. Single-stranded DNA fragments are isolated from the subclones and their base sequences are determined by dideoxy chain termination method. The complete nucleotide sequence of human EF-1α chromosomal gene will be determined based on the base sequence of these DNA fragments. The location of exons and introns is determined by comparing DNA sequences of human EF-1α cDNA with that of human EF-1α chromosomal gene.

Also, the transcription initiation site is determined by primer extension method using an mRNA extracted from a human cell line and a synthetic oligonucleotide which is complementary to human EF-1α cDNA. Typical TATA box found in the promoter region of human EF-1α gene was located at about 30 nucleotides upstream [underlined position in sequence (I)] of the transcription initiation site [marked position with * in sequence (I)].

The novel DNA fragment of the present invention is in no way to be taken as limiting on condition that it contains the promoter region of above-described human polypeptide chain elongation factor gene and has an expression function of a protein in mammalian cells as the host. Also, the novel DNA fragment of the present invention may include a DNA fragment containing a promoter region cf human polypeptide chain elongation factor-1α gene, a DNA fragment further comprising at least a portion of a region of about 2.5 kilo base pairs which is located immediately upstream of the initiation codon of the human polypeptide chain elongation factor-1α gene, a DNA fragment containing at least a portion of the above-described base sequence (I) and any of these DNA fragments wherein at least one base of the base sequence is modified by mutation, deletion or insertion.

These novel DNA fragments of the present invention may be obtained either by organic chemical synthesis or the method described above.

Construction of an expression plasmid using a novel DNA fragment containing a promoter region of human EF-1α gene may be performed, for example, as follows.

Cloned human EF-1α chromosomal gene is digested with EcoRI and then isolated by appropriate means such as an agarose gel electrophoresis. The isolated DNA fragment is cut with a restriction enzyme SacI which has the only one cutting site in human EF-1α gene intron 1, thus yielding two DNA fragments; one containing the promoter region, exon 1 and a part of the intron 1 and the other containing all exons excluding exon 1. Each of the two DNA fragments is isolated and subcloned into an appropriate plasmid, preferably pUC 119, which has one EcoRI recognition site and one SacI recognition site. Of the resulting two plasmids, the promoter-region-containing plasmid is cut with a restriction enzyme PstI and then treated with a nuclease Bal31. The treated fragment is then ligated with HindIII linker to make it into a circular plasmid. Some types of plasmids having different insertion site of HindIII, that is, a plasmid containing exon 1 and its upstream part and the other plasmid which does not contain exon 1, may be obtained depending on the degree of the Bal31 reaction.

A plasmid containing the upstream part of human EF-1α gene immediately before the initiation codon ATG in exon 2 may be constructed as follows. Firstly, one of the above-described plasmids, which contains downstream part of the gene starting with exon 2 and including all other downstream exons, is cut with a restriction enzyme BglII and treated with a nuclease Bal31. The treated fragment is then ligated with EcoRI linker to make it into a circular plasmid. In this manner, a plasmid containing a fragment starting from the SacI cut site to the site immediately before the initiation codon is obtained. The plasmid thus obtained is digested with EcoRI, the terminal of the resulting fragment is smoothed using T4 DNA polymerase and the smooth-end is connected with HindIII linker. A human EF-1α chromosomal gene-originated SacI-HindIII fragment is isolated from the HindIII linker-connected fragment and subcloned into pUC 119. Then, the SacI-HindIII fragment subcloned into pUC 119 is re-isolated by digesting the plasmid with SacI and HindIII and inserted into the SacI-HindIII site of the previously constructed plasmid which contains the promoter region of human EF-1α gene covering the upstream part of the SacI site in intron 1. In this way, a plasmid containing promoter region of human EF-1α gene covering the upstream nucleotide sequence immediately before the initiation codon in exon 2 is constructed.

There are many methods for the measurement of the expression efficiency. It is preferable to use chloramphenicol acetyltransferase (to be referred to as CAT hereinafter) gene and the like for the purpose of easy measuring. For example, the amount of expressed CAT gene may be measured as the formation rate of acetylated product of chloramphenicol using thin-layer chromatography and the like. When a gene other than CAT is used, the expression efficiency may be measured by a fluorescence antibody technique and the like.

Practically, construction of an expression plasmid is performed by the following procedure. DNA fragments containing a promoter region of human EF-1α gene are obtained by digesting above-described various plasmids with ScaI and HindIII. A DNA fragment encoding CAT gene is obtained by cutting it out from a CAT gene-containing plasmid and the like using appropriate restriction enzymes. For example, a CAT gene-containing DNA fragment can be cut out from pSV2-CAT plasmid using HindIII and BamHI, An expression plasmid which fits for the purpose is constructed by inserting the CAT gene-containing fragment into an appropriate plasmid previously cut with BamHI, HincII and the like, together with a DNA fragment containing promoter region of human EF-1α gene.

For example, the present inventors have constructed four expression plasmids, pEF220-CAT, pEF223-CAT, pEF204-CAT and pEF321-CAT, wherein nucleotide sequences from 5' end to 220 ↑, to 223 ↑, to 204 ↑ and to 321 ↑ shown in the base sequence (I) of the DNA fragment containing promoter region of human EF-1α chromosomal gene are inserted respectively. These four plasmids, named E. coli DH5 (pEF220-CAT), E. coli DH5 (pEF223-CAT), E. coli DH5 (pEF204-CAT) and E. coli DH5 (pEF321-CAT), have been deposited by the present inventors on Mar. 2, 1989, in Fermentation Research Institute, Agency of Industrial Science and Technology, and have been assigned the designations as FERM P-10595, FERM P-10596, FERM P-10594 and FERM P-10597, respectively.

Further, these four plasmids have been transferred to the INTERNATIONAL DEPOSITARY AUTHORITY Nov. 8, 1989, and have been assigned the designations as FERM BP-2647 (from FERM P-10595), FERM BP-2648 (from GERM P-10596), FERM BP-2646 (from FERM P-10594) and FERM BP-2649 (from FERM P-10597), respectively.

In addition, production of a desired physiologically active substance may be achieved using any of these expression plasmids of the present invention by substituting a gene encoding a physiologically active substance for the CAT gene in the expression plasmids. Substitution of a gene may be performed by applying necessary treatments commonly used in this field of studies. For example, it is preferable to remove the plasmid-originated HindIII recognition site in advance. Also, it is preferable to keep intact the poly (A) signaling region in order to ensure poly (A) addition to messenger RNA within cells.

EXAMPLES

Examples of the present invention are given below by way of illustration, and not by way of limitation.

Cell culture media used in the following examples are shown below. Each medium was prepared according to the preparation protocol attached to the medium article and used after adding kanamycin to the final concentration of 60 mg/l, except for Eagle's MEM medium.

| | |
|---|---|
| DM-160AU medium | (Kyokuto Pharmaceutical Industrial Co., Ltd.) |
| Eagle's MEM medium (MEM) | (Nissui Pharmaceutical Co., Ltd.) |
| Dulbecco's Modified Eagle's medium (DMEM) | (Nissui Pharmaceutical Co., Ltd.) |
| Ham's F12 medium (Ham's F12) | (Nissui Pharmaceutical Co., Ltd.) |
| RPMI 1640 medium | (Nissui Pharmaceutical Co., Ltd.) |

Unless otherwise stated, commonly used abbreviations in this field of study are used in the following descriptions. Each experiment in the following examples is based on the common gene manipulation techniques which can be performed in accordance with any commonly used manual, such as *Molecular Cloning, A Laboratory Manual* (Maniatis et al., Cold Spring Harbor Laboratory, 1982) and Labomanual Gene Technology (written in Japanese; M. Muramatsu, Maruzen Co., Ltd., 1988).

EXAMPLE 1

Isolation and identification of human EF-1α chromosomal gene (1) Isolation of human EF-1α cDNA Plasmid pNK1 containing yeast EF-1α chromosomal gene which had been constructed by K. Nagashima et al., (*Gene*, vol. 45, p. 265, 1986) was digested with ClaI and HindIII, and the ClaI-HindIII fragment (ca. 1 kilo base pairs) was isolated on agarose gel electrophoresis. A probe was prepared by labeling the fragment thus isolated with [$^{32}$P] by nick translation using [α-$^{32}$P]dCTP.

A cDNA library of human fibroblast GM637 constructed by H. Okayama and P. Berg (*Mol. Cell. Biol.*, vol. 3, p. 280, 1983) was kindly provided by Dr. Okayama at National Institute of Health. About 40,000 colonies obtained from the library were screened by colony hybridization using the above-described probe, in accordance with the conditions reported by S. Nagata et al., (*Proc. Natl. Acad. Sci. U.S.A.*, vol. 80, p. 6192, 1983).

Colonies replicated on a nitrocellulose filter were hybridized at 28° C. with the probe which has been heated at 95° C. for 5 min and immediately cooled. After washing, the filter was applied to an autoradiography in order to screen clones The length of human EF-1α cDNA in positive clones thus obtained was analyzed by agarose gel electrophoresis, and a plasmid containing the longest cDNA (ca. 1.8 kilo base pairs) was designated pAN7. The complete base sequence of human EF-1α cDNA was then determined by dideoxy chain termination method. The complete base sequence of human EF-1α cDNA thus obtained is shown in FIG. 1.

The result showed that the coding region for the human EF-1α cDNA gene consisted of 1386 base pairs and its base sequence was identical with the base sequence of the coding region for a human EF-1α cDNA which has been reported by J. H. G. M. Brands et al., (*Eur. J. Biochem.*, vol. 155, p. 167, 1986).

(2) Cloning of human EF-1α chromosomal gene

For the purpose of isolating human EF-1α chromosomal gene, human gene libraries were screened using the human EF-1α cDNA obtained in Example 1-(1) as the probe. Human gene libraries constructed with human fetal liver DNA (R. M. Lawn et al.; *Cell*, vol. 15, p. 1157, 1978) and human placenta DNA (H. Matsushime et al.; *Mol. Cell. Biol.*, vol. 6, p. 3000, 1986) were provided by Dr. T. Maniatis at Harvard University and Dr. M. Shibuya at Institute of Medical Science, University of Tokyo, respectively. A probe was prepared by isolating a BamHI fragment (ca. 2 kilo base pairs) of human EF-1α cDNA from the above-described plasmid pAN7 and labeling the fragment with [$^{32}$P] by nick translation under the same conditions as described in Example 1-(1).

A total of about 1,500,000 plaques obtained from both human gene libraries were screened by plaque hybridization, and 218 positive clones were obtained. Five of the positive clone-containing plaques were selected at random, and their λ DNAs carrying chromosomal DNA fragments were prepared Although chromosomal DNA fragments from these five clones hybridized strongly with human EF-1α cDNA probe, the restriction enzyme digestion mapping and the nucleotide sequencing analysis showed that they did not contain any intron but several mutations, deletions or insertions. On the basis of these results, these chromosomal DNA fragments were considered to be pseudogenes of human EF-1α.

For the purpose of isolating and identifying active human EF-1α chromosomal gene, a nucleotide sequence consisting of 18 bases (5'-GATAACAATGCATCGTAA-3') in the 3' non-coding region of the human EF-1α cDNA (a sequence located at about 120 bases downstream of the termination codon) was synthesized using a DNA synthesizer (Applied Biosystems, Model 380A). The oligonucleotide thus synthesized was labeled with [$^{32}$P] using T4-polynucleotide kinase and [γ-$^{32}$P] and used as the probe. Using this probe, 70 of the above-described positive clones were screened again by means of plaque hybridization. As the result, 5 of the tested clones were found positive. It was confirmed that one of the 5 positive clones, named λEFg 58, contained about 7 kilo base pairs of EcoRI fragment, and this fragment contained human EF-1α chromosomal gene, because the fragment hybridized with the human EF-1α cDNA probe.

(3) Sequencing of human EF-1α chromosomal gene

The human EF-1α chromosomal DNA fragment cloned into λEFg 58 obtained in Example 1-(2) was cut out with EcoRI and isolated on agarose gel electrophoresis. The 7 kilo base pair EcoRI fragment was subcloned at the EcoRI site of pUC 119 and the resulting plasmid was designated pEFg 1.

Next, the plasmid pEFg 1 was treated with various restriction enzymes and restriction enzyme cut sites were determined based on the the number and moving rate of bands of the digests on agarose gel electrophoresis, in order to construct a restriction enzyme digestion map of human EF-1α chromosomal gene. For the purpose of determining base sequence of human EF-1α chromosomal gene, plasmid pEFg 1 was cut with various restriction enzymes and DNA fragments were subcloned into M13 mp8 or M13 mp9. Single-stranded DNA was isolated according to a commonly used method and the base sequence was determined by dideoxy chain termination method. As the result, it was confirmed that the DNA fragment cloned into plasmid pEFg 1 was the human EF-1α chromosomal gene, because base sequence of the DNA fragment was completely identical with that of the human EF-1α cDNA. A restriction enzyme digestion map of human EF-1α chromosomal gene and direction of the sequencing are shown in FIG. 2, and a base sequence of about 4.7 kilo bases starting at SmaI site is shown in FIG. 3.

(4) Structure of human EF-1α chromosomal gene

The human EF-1α cDNA obtained in Example 1-(1) and the human EF-1α chromosomal gene obtained in Example 1-(3) were compared in order to determine the position of exons and introns. As the result, it was found that the chromosomal gene comprised 8 exons and 7 introns (FIG. 2).

The transcription initiation site of human EF-1α gene was determined by the primer extension method. A single-stranded cDNA fragment was synthesized using 5 μg of mRNA obtained from human HL-60 cells, 5 pmol of [$^{32}$P]-labeled oligonucleotide (5'-TGTGTTCTGGCGGCAAACCCGTTG-3') which is complementary to the nucleotide positions 584 to 607 shown in FIG. 3, 25 units of AMV reverse transcriptase and 40 units of RNase inhibitor. The transcription initiation site (the position marked with * in FIG. 3) was determined by analyzing the single-stranded cDNA fragment thus obtained by means of 7 M urea-containing 8% polyacrylamide gel electrophoresis.

On the basis of these results, it was found that exon 1 consisted of 33 bases, the initiation codon ATG was located in exon 2, and the sequence of intron 1 between the exons 1 and 2 consisted of 943 bases.

EXAMPLE 2

Construction of CAT gene expression plasmid containing promoter region of human EF-1α gene (1) Construction of plasmids pEF-2 and pEF-3.

Figure 4:
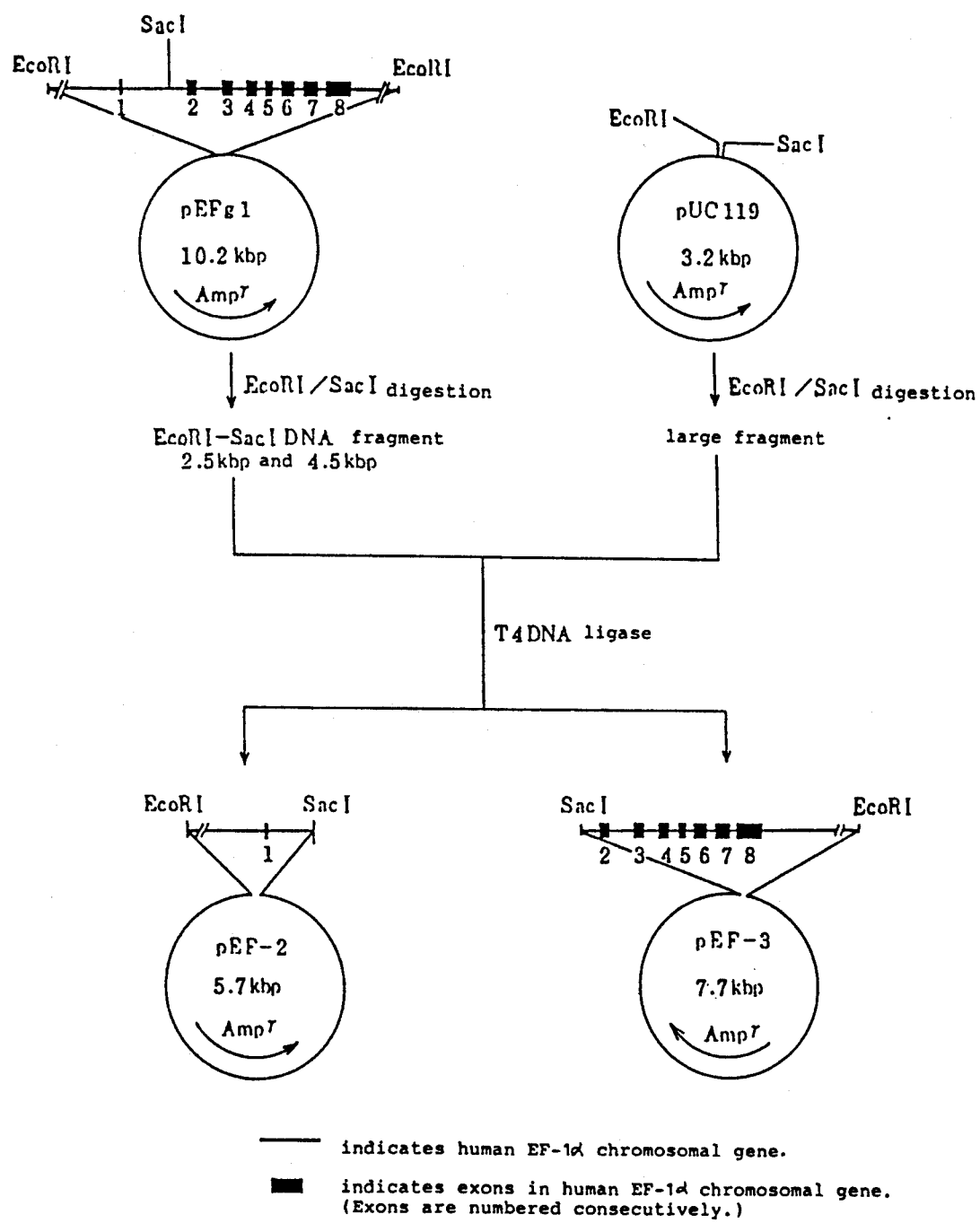

A flow diagram for the construction of these plasmids is shown in FIG. 4. The human EF-1α gene-containing EcoRI fragment (ca. 7 kilo base pairs) in plasmid pEFg 1 was digested with SacI and EcoRI, and two DNA fragments (about 2.5 and 4.5 kilo base pairs, respectively) were isolated on agarose gel electrophoresis. Each of the two DNA fragments was subcloned at the site between EcoRI and SacI of plasmid pUC 119. One plasmid containing a promoter region of human EF-1α gene and exon 1 was designated pEF-2 and the other plasmid containing exons 2 to 8 was designated pEF-3.

(2) Construction of plasmids pEF-220, pEF-223 and pEF-204.

Figure 5:
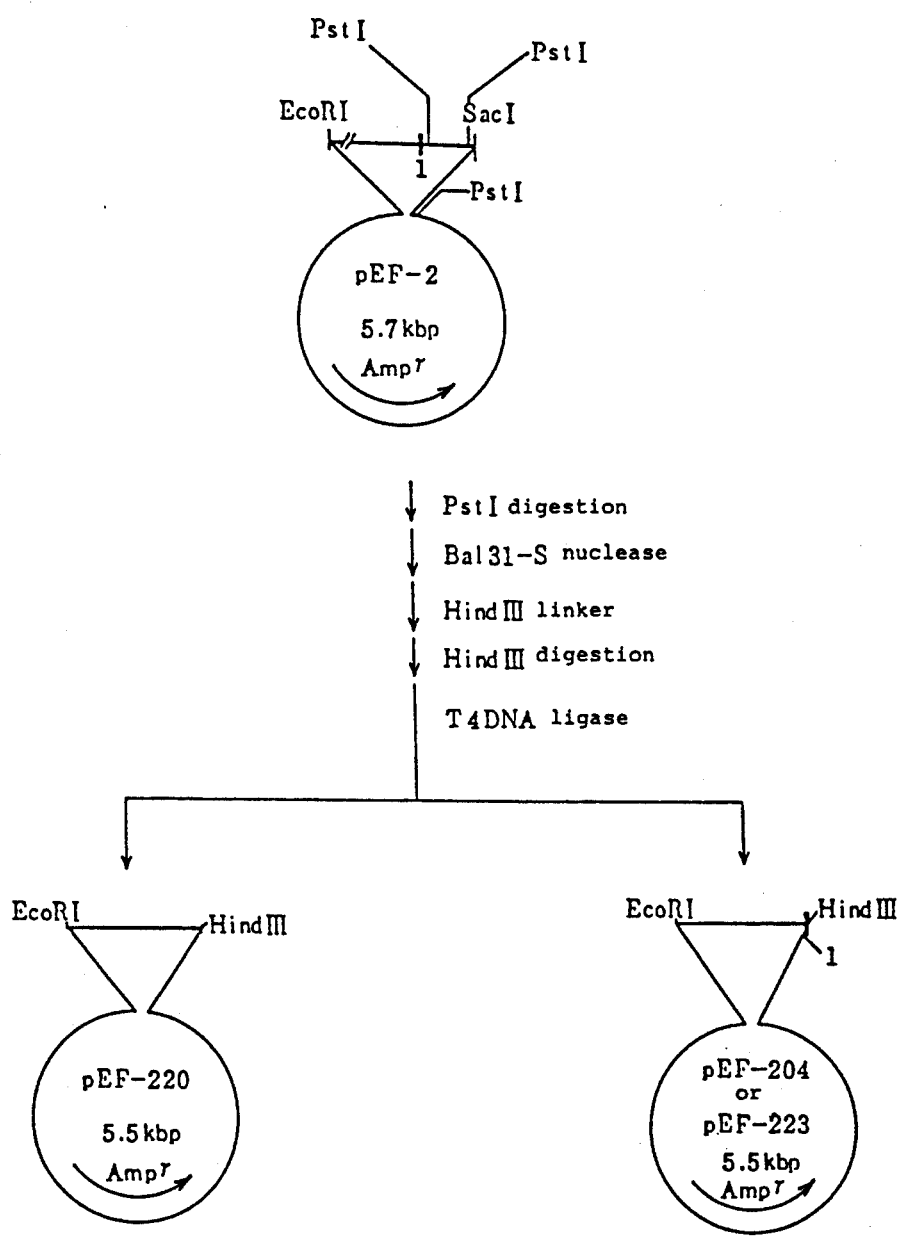
FIG. 5 shows a flow diagram for the construction of plasmids pEF-220, pEF-223 and pEF-204.

A flow diagram for the construction of these plasmids is shown in FIG. 5. A 10 μg portion of plasmid pEF-2 prepared in Example 2-(1) was digested with PstI and incubated at 30° C. for 10 min in the presence of 3 units of Bal31-S nuclease (Takara Shuzo Co. Ltd.). To the Bal31-S digested DNA fragments 1 μg of 5'-phosphorylated HindIII linker pCAAGCTTG (Takara Shuzo Co., Ltd.) was ligated using T4 DNA ligase. Plasmids containing HindIII recognition site were obtained by digesting the linker-added fragment with HindIII and making the digests into circular plasmids using T4 DNA ligase. Although the inserted position of HindIII recognition region into these plasmids varied, the region of human EF-1α chromosomal DNA in each plasmid was revealed precisely by determining base sequence of each plasmid by dideoxy chain termination method using the plasmid DNA as the template (upstream-directed sequencing started from HindIII site). Of these, following 3 plasmids were selected for used in the construction of expression plasmid; that is, a plasmid designated pEF-220 containing an upstream region of human EF-1α chromosomal gene between the EcoRI site and a site [shown as "220 ↑" in sequence (I)] 21 bases upstream of the transcription initiation site, a plasmid designated pEF-223 containing an upstream region of the gene between the EcoRI site and a site [223 ↑ in sequence (I)] 8 bases downstream of the transcription initiation site and a plasmid designated pEF-204 containing an upstream region of the gene between the EcoRI site and a site [204 ↑ in sequence (I)] 24 bases downstream of the transcription initiation site.

(3) Construction of plasmid pEF-321.

Figure 6:
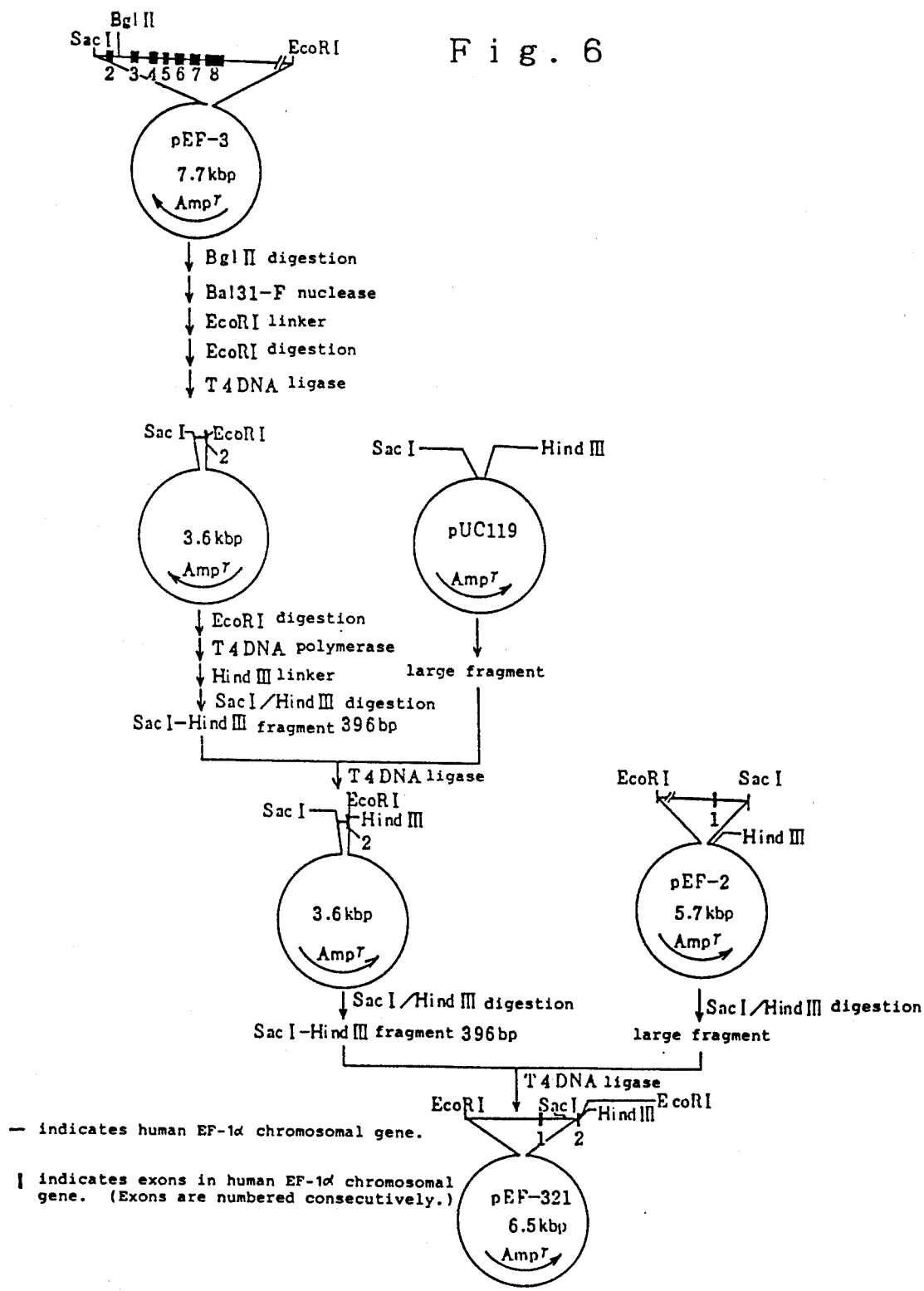
FIG. 6 shows a flow diagram for the construction of plasmid pEF-321.

A flow diagram for the construction of this plasmid is shown in FIG. 6. A 5 μg portion of plasmid pEF-3 prepared in Example 2-(1) was digested with BglII and incubated at 30° C. for 8 min in the presence of 1.3 unit of Bal31-F nuclease (Takara Shuzo Co., Ltd.). To the Bal31-F digested DNA fragment 1 μg of 5'-phosphorylated EcoRI linker pGGAATTCC (Takara Shuzo Co., Ltd.) was ligated using T4 DNA ligase. Plasmids containing a region between SacI site and a site in exon 2 were obtained by digesting the linker-added fragment with EcoRI and making the digests into circular plasmids using T4 DNA ligase. The inserted position of EcoRI recognition region was determined by the same sequencing technique as described in Example 2-(2), and a plasmid containing a region between the SacI site and a site 10 bases downstream of the 5' end of exon 2 [a site marked with 321 ↑ in sequence (I)] was selected.

The plasmid thus obtained was cut with EcoRI, and the resulted fragment was smooth-ended using T4 DNA polymerase and ligated with HindIII linker in the same manner as described in Example 2-(2). A SacI-HindIII fragment (396 base pairs) containing a portion of exon 2 (10 base length) was isolated from the linker-added DNA fragment and inserted between the SacI site and HindIII site of pUC 119 using T4 DNA ligase. Plasmid pEF-321 was obtained by re-isolating the SacI-HindIII fragment from the resulted plasmid and inserting the fragment between the SacI site and HindIII site of plasmid pEF-2 prepared in Example 2-(1) using T4 DNA ligase. The plasmid pEF-321 contains a region of human EF-1α chromosomal gene ranging from the upstream EcoRI site of the gene to the first 10 bases in the exon 2 (a site 21 base-upstream of the initiation codon ATG).

(4) Construction of plasmids pEF204-CAT, pEF223-CAT, pEF220-CAT and pEF321-CAT.

Figure 7:
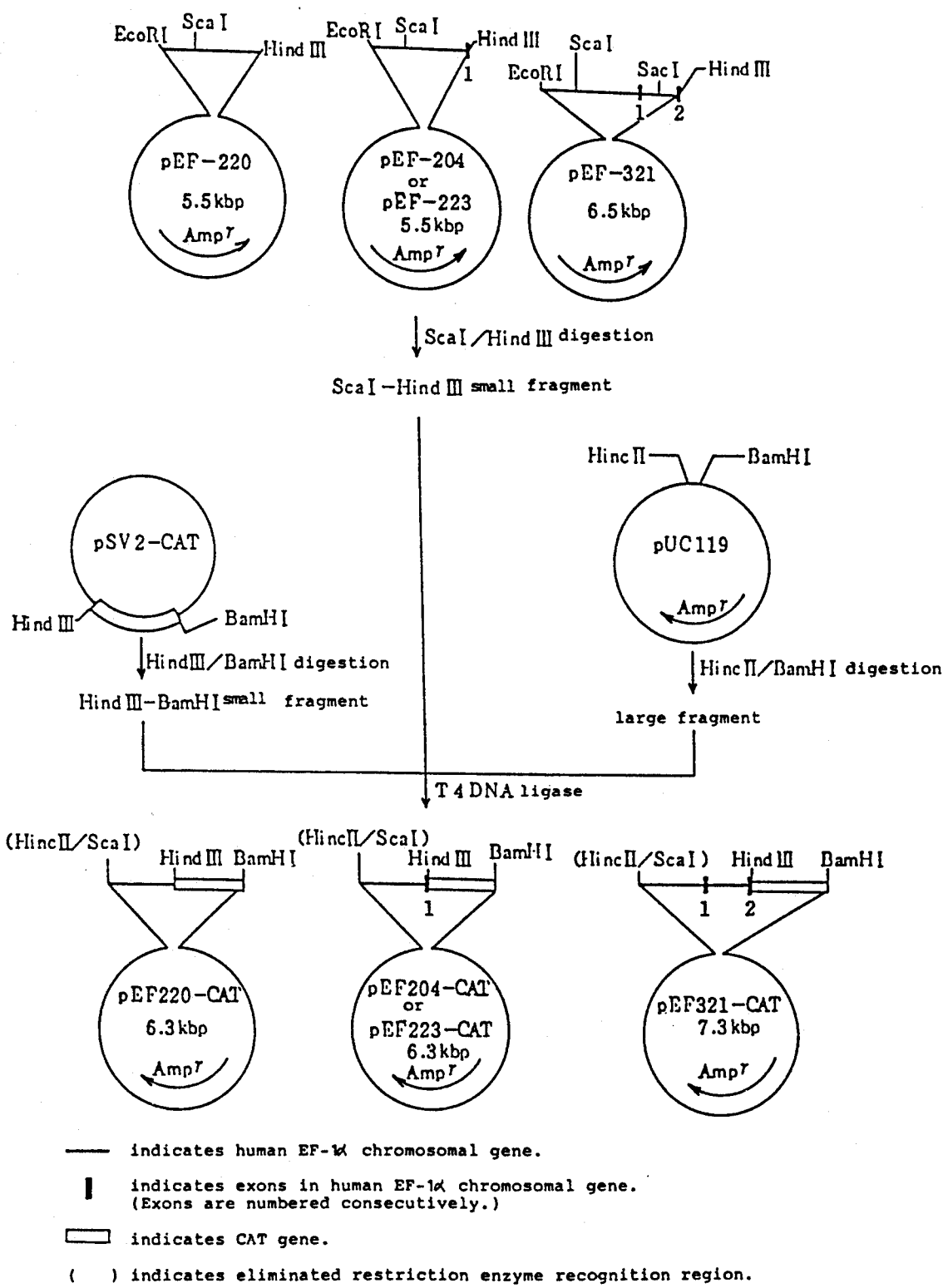
FIG. 7 shows a flow diagram for the construction of plasmids pEF220-CAT, pEF223-CAT, pEF204-CAT and pEF321-CAT.

A flow diagram for the construction of these plasmids is shown in FIG. 7. Plasmid pEF-220, pEF-223 or pEF-204 obtained in Example 2-(2) or plasmid pEF-321 obtained in Example 2-(3) was digested with ScaI and HindIII and a ScaI-HindIII fragment containing a promoter region of human EF-1α gene was isolated. CAT gene was isolated as a DNA fragment consisting of about 1.6 kilo base pairs from plasmid pSV2-CAT (C. M. Gorman et al.; *Mol. Cell. Biol.*, vol. 2, p. 1044, 1982) kindly provided by Dr. P. Berg at Stanford University, by digesting the plasmid with HindIII and BamHI.

These two DNA fragments and a HincII-BamHI large fragment (3.2 kilo base pairs) obtained from plasmid pUC 119 were connected using T4 DNA ligase. Plasmids pEF220-CAT, pEF223-CAT, pEF204-CAT and pEF321-CAT were prepared in this way. Each ScaI-HindIII fragment of these plasmids contains additional sequence of about 950 base pairs attached to the 5'-end of the base sequence (I).

EXAMPLE 3

Figure 8:
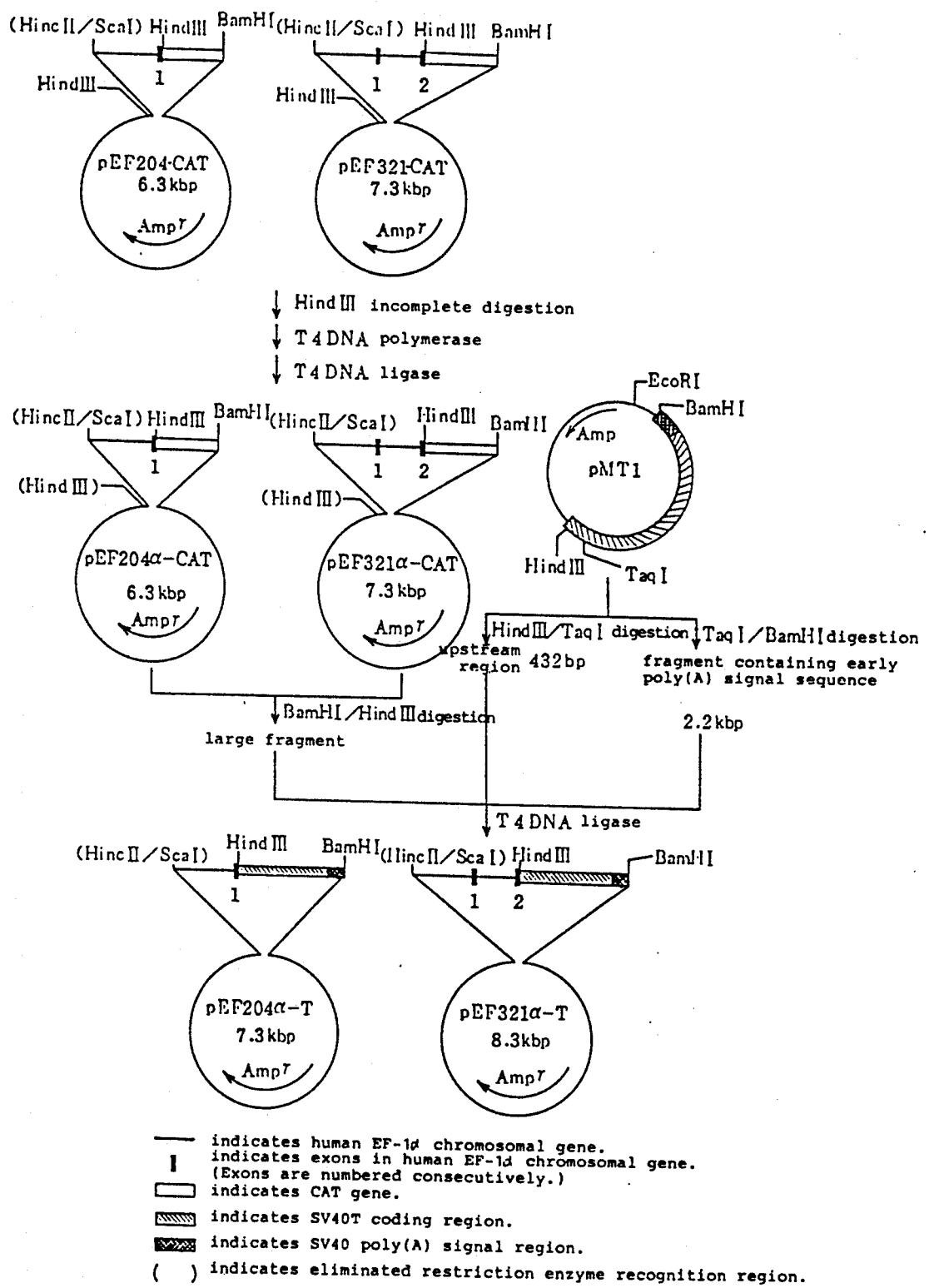
FIG. 8 shows a flow diagram for the construction of plasmids pEF204α-T and pEF321α-T.

Construction of SV40 T antigen expression plasmids containing promoter region of human EF-1α gene A flow diagram for the construction of these plasmids is shown in FIG. 8.

(1) Construction of plasmids pEF204α-CAT and pEF321α-CAT.

For the purpose of removing the pUC 119-originated HindIII recognition site selectively, incomplete digestion of plasmids pEF204-CAT and pEF321-CAT were performed by incubating 4 μg of each plasmid at 37° C. for 10, 15, 25 or 40 min in the presence of 6 units of HindIII. DNA fragments produced by digestion of the plasmid at only one cut site were isolated and purified on agarose gel electrophoresis. The purified DNA fragments were smooth-ended using T4 DNA polymerase and then ligated with T4 DNA ligase. These plasmids thus obtained were digested with HindIII and BamHI and a plasmid from which the CAT gene-originated DNA fragment (1.6 kilo base pairs) was able to be cut out by the digestion was selected. In this way, plasmids named pEF204α-CAT and pEF321α-CAT were obtained from pEF204-CAT and pEF321-CAT, respectively.

(2) Construction of plasmids pEF204α-T and pEF321α-T.

Plasmid pMT1 containing the coding region of SV40 T antigen (S. Sugano et al.; J. Virol., vol. 52, p. 884, 1984) was digested with HindIII and TaqI and an upstream fragment (432 base pairs) of the coding region of SV40 T antigen was isolated. Separately from this experiment, plasmid pMT1 was digested with TaqI and BamHI and a downstream fragment (2.2 kilo base pairs), containing early poly (A) signaling sequence, of the coding region of SV40 T antigen was isolated.

The CAT gene in each of the plasmids pEF204α-CAT and pEF321α-CAT prepared in Example 3-(1) was removed by digesting each plasmid with HindIII and BamHI. The region between HindIII site and BamHI site thus emptied was inserted with both HindIII-TaqI and TaqI-BamHI fragments described above. In this manner, plasmids pEF204α-T and pEF321α-T containing entire coding region of SV40 T antigen were constructed.

EXAMPLE 4

Figure 9:
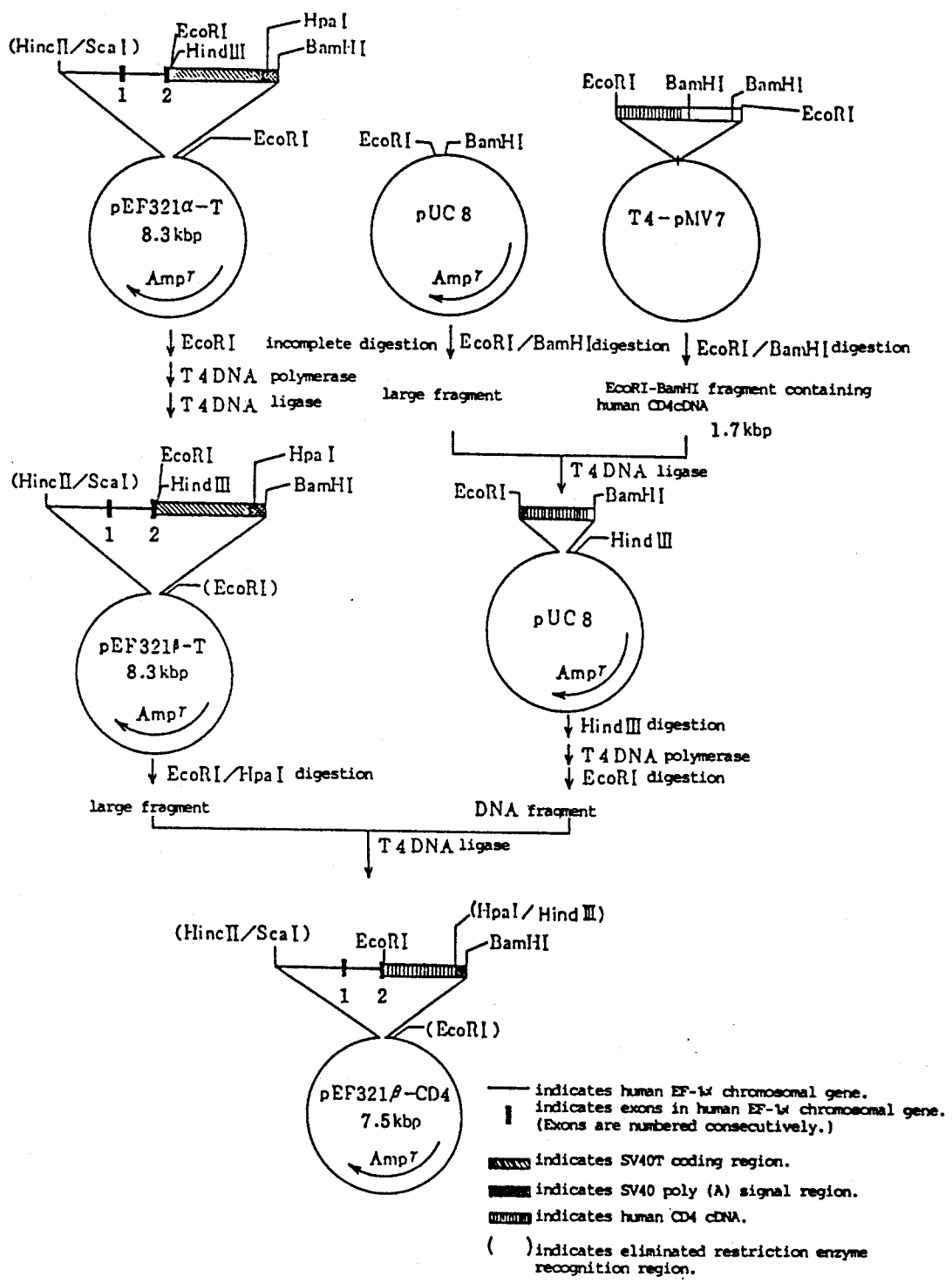
FIG. 9 shows a flow diagram for the construction of plasmid pEF321β-CD4.

Construction of human CD4 cDNA expression plasmid containing promoter region of human EF-1α gene A flow diagram for the construction of this plasmid is shown in FIG. 9. Human CD4 cDNA (about 1.7 kilo base pairs) was cut out as an EcoRI-BamHI fragment from plasmid T4-pMV7 containing human CD4 cDNA (P. J. Maddon et al.; Cell, vol. 47, p. 333, 1986) and inserted into plasmid pUC 8. The resulted plasmid was digested with HindIII, smooth-ended using T4 DNA polymerase and again digested with EcoRI, in order to isolate a CD4 cDNA fragment. A plasmid pEF321β-T was obtained by eliminating pUC 119-originated EcoRI recognition site from the plasmid pEF321α-T prepared in Example 3 by using the same method described in Example 3-(1). A plasmid, named pEF321β-CD4, was constructed by digesting the plasmid pEF321β-T with EcoRI and HpaI and then ligating a large fragment isolated from the digested fragments with the above-described human CD4 cDNA fragment using T4 DNA ligase.

EXAMPLE 5

Expression of CAT gene

Expression efficiencies of four expression plasmids containing promoter region of human EF-1α gene, pEF220-CAT, pEF223-CAT, pEF204-CAT and pEF321-CAT, were compared with those of other expression plasmids pSV2-CAT and pSRα-CAT (kindly provided by Dr. Takebe at National Institute of Health (Japan)).

(1) Transfection of expression plasmids on to various cell lines.

The following shows cell lines used in this experiment and conditions for the culturing of each cell line, including medium, cell density as the inoculum (the number of cells per 10 cm² plate medium) and culture time.
a) CHO-K1 (Chinese hamster ovary cell, ATCC CCL61) 10% FCS-containing Ham's F12 medium $1.2 \times 10^6$ cells, 48 h
b) IMR-32 (human neuroblast cell, ATCC CCL127) 10% FCS-containing DMEM medium $2.0 \times 10^6$ cells, 48 h
c) 3Y1 (rat fibroblast cell) 8% FCS-containing DMEM medium $2.0 \times 10^6$ cells, 24 h
d) CV-1 (African green monkey kidney cell, ATCC CCL70) 8% FCS-containing DMEM medium $2.0 \times 10^6$ cells, 24 h
e) COS-1 (African green monkey kidney cell transformed by SV40, ATCC CRL1650) 8% FCS-containing DMEM medium $2.0 \times 10^6$ cells, 24 h
f) T22 (monkey kidney cell transformed by SV40) 8% FCS-containing DMEM medium $2.0 \times 10^6$ cells, 24 h
g) BrA2-227 (rat brain cell line immortalized by SV40 mutant T antigen A2) 8% FCS-containing DMEM medium $2.0 \times 10^6$ cells, 24 h
h) BrA2-SS (rat brain cell line immortalized by SV40 mutant T antigen A2) 8% FCS-containing DMEM medium $2.0 \times 10^6$ cells, 24 h
i) JTC-16.P3 (rat hepatoma cell, JCRB 0714) 1% FCS-containing DM-160AU medium About 50% confluent, 48 h
j) NY (human oesteosarcoma cell, JCRB 0614) 8% FCS-containing MEM medium $2.0 \times 10^6$ cells, 72 h
k) MT-1 (human T cell leukemia cell, JCRB 0063) 10% FCS-containing RPMI 1640 medium An aliquot of cell suspension containing $2 \times 10^6$ cells was used Each cell line was cultured under these conditions prior to the addition of plasmid DNA, and the culture medium was renewed about one hour before the addition of plasmid DNA.

A 0.45 ml portion of solution containing 10 to 20 μg of each plasmid DNA was mixed with 50 μl of 2.5M CaCl₂, stirred while 0.5 ml of 2×HBS (280 mM NaCl/50 mM HEPES/2.8 mM Na₂HPO₄, pH 7.05) was dripped and then maintained at room temperature for 10 min. The DNA precipitate thus obtained was applied to the above-described medium containing cultured cells and incubated for 6 h. The cells were washed with about 10 ml of PBS⁻ and treated with 20% DMSO/medium for 3 min in order to obtain transfectants. Transfectants thus obtained were washed with PBS⁻, suspended in the medium and stored at 37° C. in the presence of 5% CO₂.

(2) CAT assay

CAT assay was performed in accordance with the method of C. M. Gorman et al. (*Mol. Cell. Biol.*, vol. 2, p. 1044, 1982). Each cell line was cultured at 37° C. for 48 h in the presence of 5% $CO_2$, and the cultured cells were rinsed twice with PBS⁻ and harvested by centrifugation at 1000 rpm for 3 min. The cells were suspended in 200 μl of 0.25M Tris-HCl (pH 7.8), subjected to three cycles of freeze-thaw and then disrupted by sonication. The sonicated suspension was centrifuged at 15,000 rpm for 15 min at 4° C., and an aliquot of the resulting supernatant was assayed for protein content in accordance with the method of Bradford et al. (*Anal. Biochem.*, vol. 72, p. 248, 1976).

Based on the result of the protein assay, a supernatant which seemed to have the protein content of about 150 μg was selected, with the exception of 2 μg, 18 μg, 6 μg, 41 μg and 760 μg in the case of CHO-K1, NY, JTC-16.P3, MT-1 and IMR-32, respectively. An aliquot of the supernatant thus selected was mixed in a final volume of 238 μl, with 0.2 μCi of [$^{14}$C] chloramphenicol (Amersham)/1 mM acetyl-CoA/0.25M Tris-HCl (pH 7.8). After incubation at 37° C. for 2 h (30 min in the case of CHO-K1 and NY and 40 min in JTC-16.P3), contents of the reaction solution were extracted with ethyl acetate and then solidified by evaporation. The solid was dissolved again in 15 μl of ethyl acetate and spotted on a silica gel thin layer plate (20 cm in length, a product of Merck & Company, Inc.). The chromatography was performed using chloroform/methanol (95:5) system as the development solvent. The plate was dried when the solvent reached a level 13 cm from the upper end. An X-ray film was then laid on top of the thin layer plate and kept for 18 to 20 h (3 days in the case of MT-1) to take an autoradiograph.

The amount of CAT expressed by each transfectant was estimated based on the ratio of acetylated [14C] chloramphenicol. In addition, the radioactivity on the thin layer plate was directly counted by using a Radio Analytic Labeling System (trade name of a product of AMBIS System Inc.) as a quantitative measuring method.

Figure 10:
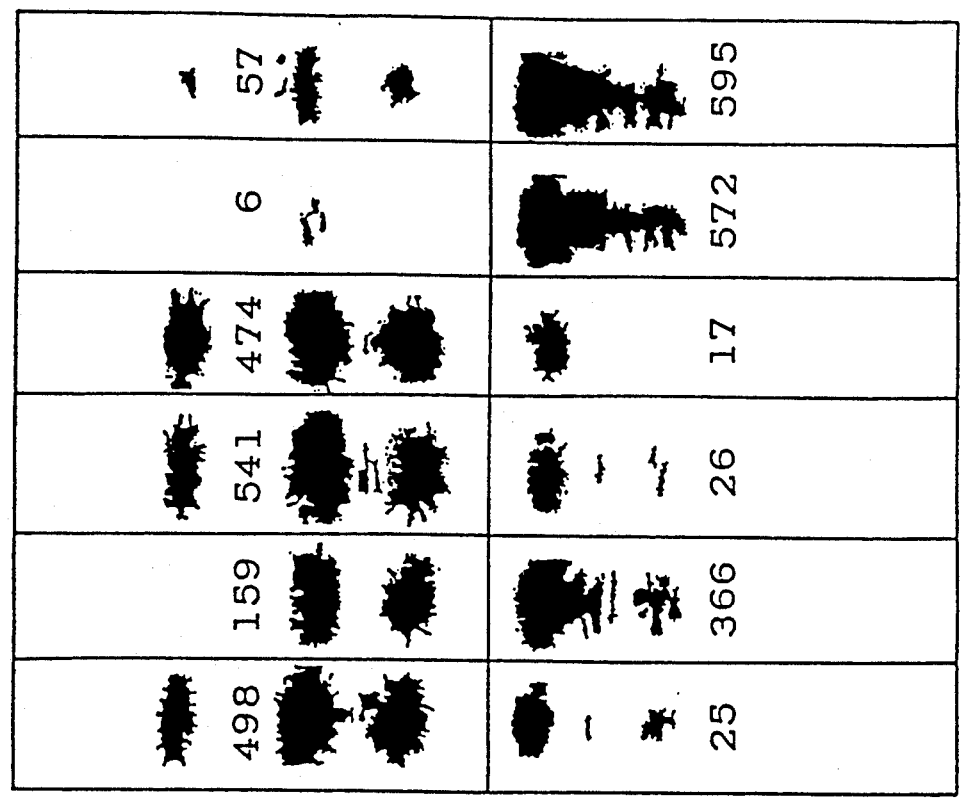
FIG. 10 shows a result of CAT assay in IMR-32 cells.

As a typical example, results of the measurement of the expression efficiency of CAT gene in IMR-32 cells by using the Radio Analytic Labeling System are shown in FIG. 10. Each number shown in the figure indicates the degree of the radioactivity of [$^{14}$C] chloramphenicol or acetylated [$^{14}$C] chloramphenicol. The ratio of the acetylated [14C] chloramphenicol can be expressed as (acetylated product)/(acetylated product + unchanged material). On the basis of these results, it was found that all of the four expression plasmids containing promoter region of human EF-1α gene had high expression efficiency, even in the case of human neuroblastoma cell (IMR-32) in which the efficiency of SV40 promoter-containing expression plasmid was remarkably low. In IMR-32 cell, the exon 2-containing pEF321-CAT was about 100 fold and about 10 fold more higher in the expression efficiency compared to pSV2-CAT and pSRα-CAT, respectively.

The ratio of acetylated products by each expression plasmid is summarized in Table 1.

TABLE 1

| | Comparison of expression efficiencies of CAT gene. | | | | | |
|---|---|---|---|---|---|---|
| | Examples | | | | Comparative Examples | |
| | pEF220-CAT | pEF223-CAT | pEF204-CAT | pEF321-CAT | pSV2-CAT | pSRα-CAT |
| IMR-32 | 30 | 95 | 95 | 97 | 1 | 9 |
| CHO-K1 | 3 | 12 | 17 | 26 | 14 | |
| 3Y1 | | | 66 | 95 | 6 | 94 |
| JTC-16.P3 | | | 10 | 26 | 7 | 33 |
| NY | | | 4 | 9 | 2 | 6 |
| MT-1 | | | 1 | 5 | 1 | 1 |
| BrA2-227 | | | | 39 | 8 | 35 |
| BrA2-SS | | | | 96 | 47 | 93 |
| CV-1 | | | | 84 | 5 | |
| COS-1 | | | | 98 | 34 | |
| T22 | | | | 99 | 75 | |

Blanks: not measured.

Comparison of expression efficiencies of the four expression plasmids containing promoter region of human EF-1α gene in CHO-K1 and IMR-32 cells revealed the following order of expression level: pEF321-CAT > pEF204-CAT, pEF223-CAT > pEF220-CAT. In addition, the expression efficiency of the plasmid pEF321-CAT which showed the highest expression efficiency in both CHO-K1 and IMR-32 cells was similar to or higher than those of the two SV40 promoter-containing plasmids in all tested cell lines.

EXAMPLE 6

Expression of SV40 T antigen gene

Figure 11:
FIGS. 11 to 15 are immunofluorescence microphotographs showing the distribution of expressed proteins within cells. In particular.
Figure 12:
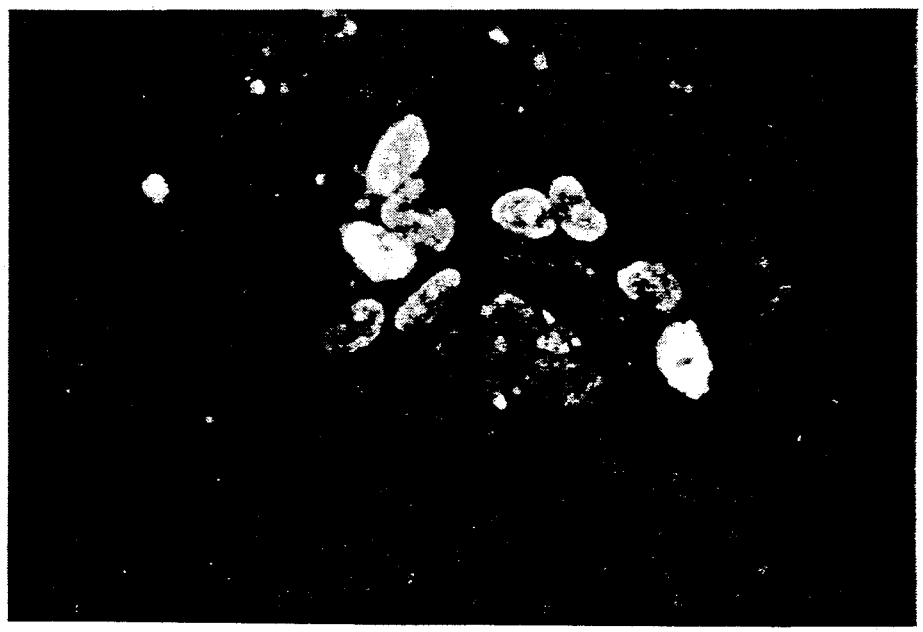

Transfection of plasmids pEF204α-T, pEF321α-T and pMT1 on to IMR-32 cells were performed in accordance with the procedure described in Example 5-(1). At 48 hours after the transfection reaction, the cells were fixed by using a mixture of ethanol and acetone (1:1) at −20° C. for 18 min and subjected to the immunofluorescence assay. As the first antibody, a hamster antiserum specific for SV40 T antigen was prepared as follows. About $2 \times 10^6$ SV40 transformant cells were inoculated subcutaneously to a three- to four-month-old hamster and the individual was reared further (generally for 2 to 6 months) until the formation of tumor was completed. After fasting for one day, whole blood of the hamster was collected in order to isolate an antiserum preparation. The fixed cells described above were incubated with the antiserum thus obtained at 37° C. for 1 h. The cells were then washed with PBS⁻ and incubated with FITC-labeled rabbit anti-hamster IgG (a product of FUJIREBIO Inc.) at 37° C. for 1 h. After washing the resulting cells with PBS⁻, the fluorescence was measured using a reflected light fluorescence microscope (Model BH2, Olympus Optical Co., Ltd.). As the result, the expression of T antigen was detected in the cells transfected with plasmids pEF204α-T and pEF321α-T as shown in FIGS. 11 and 12, but not in the cells transfected with plasmid pMT1.

EXAMPLE 7

Measurement of the stability of expression plasmids

Transfection of plasmids pEF204α-T, pEF321α-T and pMT1 on to 3Y1 cells were performed in the same manner as described in Example 6. At 24 hours after the transfection culturing, the cells were replated using a trypsin solution (0.05% trypsin/PBS−) and cultured further at 37° C. for one month in the presence of 5% $CO_2$.

As the result, all three groups of the cells transfected with pEF204α-T, pEF321α-T and pMT1 plasmid DNAs formed many high density foci. The number of focus was high in the cells transfected with plasmid pEF204α-T or plasmid pEF321α-T compared to the cells transfected with pMT1 plasmid.

Figure 13:
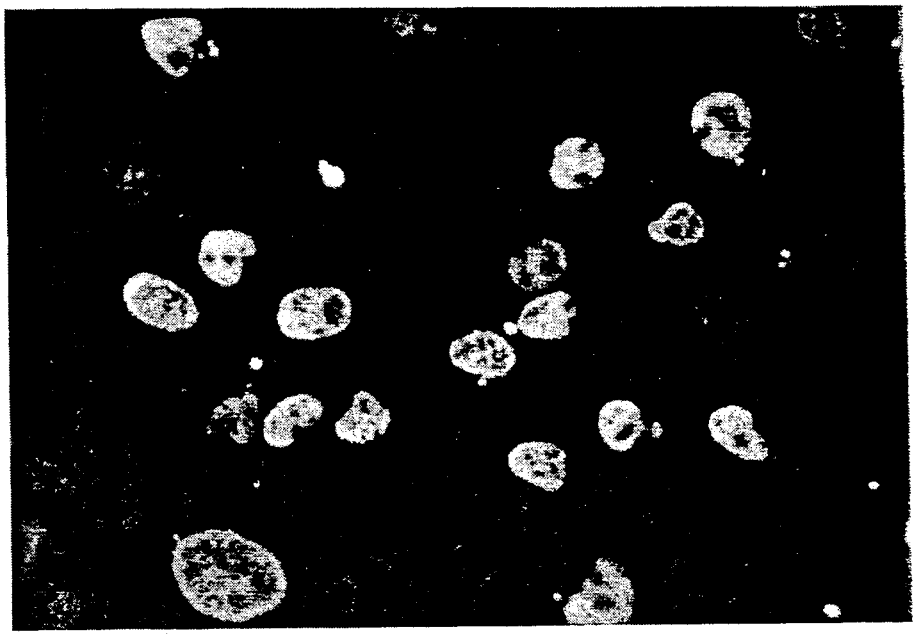
Figure 14:
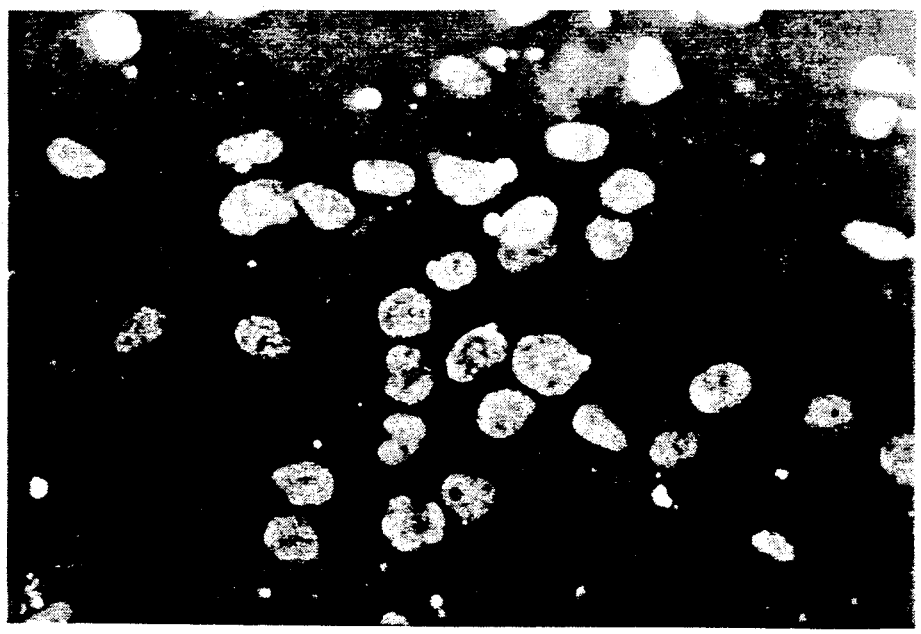

Single focus was isolated from each group of the cells, treated with the trypsin solution, replated, and then subjected to the immunofluorescence assay in accordance with the procedure described in Example 6. As shown in FIGS. 13 and 14, T antigen was detected in the cell nucleus of the cells transfected with pEF2-04α-T or pEF321α-T plasmid DNA, which indicated that these plasmid DNAs were maintained stably for one month in the cells.

EXAMPLE 8

Expression of human CD-4 gene

Plasmid pEF321β-CD4 was transfected on to CHO-K1 cell in accordance with the procedure described in Example 6. Immunofluorescence assay was performed according to Example 6 using a mouse monoclonal antibody specific for human CD4 (OKT4, a product of Ortho Diagnostic Systems K. K.) as the first antibody and an FITC-labeled rabbit anti-mouse IgG (a product of Medical & Biological Laboratories Co., Ltd.) as the second antibody.

Figure 15:

Since the human CD4 protein was detected in the cellular membrane of the transfected cells as shown in FIG. 15, expression of human CD4 by the plasmid pEF321β-CD4 in CHO-K1 cell was confirmed.

As have been described in detail in the foregoing, the present inventors have developed a novel DNA fragment containing the promoter region of human polypeptide chain elongation factor-1α and new expression plasmids containing said DNA fragment having higher applicability to wider rage of host cells with higher expression capacity compared to the applicability and expression capacity of any expression plasmid containing commonly used promoters, such as SV40 early promoter. The present inventors have also revealed the structure described above of said DNA fragment by determining its base sequence. Since these expression plasmids of the present invention were able to be maintained stably in certain host cells at least for one month, application of said expression plasmids may render possible the production of various kinds of useful physiologically active substances efficiently for a long period using wide range of mammalian cells as the host.

What is claimed is:

1. An essentially pure DNA fragment represented by the following sequence (I):

```
CCCGGGCTGGGCTGAGACCCGCAGAGGAAGACGCTCTAGG      40
GATTTGTCCCGGACTAGCGAGATGGCAAGGCTGAGGACGG      80
GAGGCTGATTGAGAGGCGAAGGTACACCCTAATCTCAATA     120
CAACCTTTGGAGCTAAGCCAGCAATGGTAGAGGGAAGATT     160
CTGCACGTCCCTTCCAGGCGGCCTCCCCGTCACCACCCCC     200
CCCAACCCGCCCCGACCGGAGCTGAGAGTAATTCATACAA     240
AAGGACTCGCCCCTGCCTTGGGGAATCCCAGGGACCGTCG     280
TTAAACTCCCACTAACGTAGAACCCAGAGATCGCTGCGTT     320
CCCGCCCCCTCACCCGCCCGCTCTCGTCATCACTGAGGTG     360
GAGAAGAGCATGCGTGAGGCTCCGGTGCCCGTCAGTGGGC     400
AGAGCGCACATCGCCCACAGTCCCCGAGAAGTTGGGGGGA     440
GGGGTCGGCAATTGAACCGGTGCCTAGAGAAGGTGGCGCG     480
GGGTAAACTGGGAAAGTGATGTCGTGTACTGGCTCCGCCT     520
TTTTCCCGAGGGTGGGGGAGAACCGTATATAAGTGCAGTA     560
GTCGCCGTGAACGTTCTTTTTCGCAACGGGTTTGCCGCCA     600
GAACACAGGTAAGTGCCGTGTGTGGTTCCCGCGGGCCTGG     640
CCTCTTTACGGGTTATGGCCCTTGCGTGCCTTGAATTACT     680
TCCACGCCCCTGGCTGCAGTACGTGATTCTTGATCCCGAG     720
CTTCGGGTTGGAAGTGGGTGGGAGAGTTCGAGGCCTTGCG     760
CTTAAGGAGCCCCTTCGCCTCGTGCTTGAGTTGAGGCCTG     800
GCCTGGGCGCTGGGGCCGCCGCGTGCGAATCTGGTGGCAC     840
CTTCGCGCCTGTCTCGCTGCTTTCGATAAGTCTCTAGCCA     880
```

-continued

```
TTTAAAATTTTTGATGACCTGCTGCGACGCTTTTTTTCTG    920

GCAAGATAGTCTTGTAAATGCGGGCCAAGATCTGCACACT    960

GGTATTTCGGTTTTTGGGGCCGCGGGCGGCGACGGGGCCC   1000

GTGCGTCCCAGCGCACATGTTCGGCGAGGCGGGGCCTGCG   1040

AGCGCGGCCACCGAGAATCGGACGGGGGTAGTCTCAAGCT   1080

GGCCGGCCTGCTCTGGTGCCTGGCCTCGCGCCGCCGTGTA   1120

TCGCCCCGCCCTGGGCGGCAAGGCTGGCCCGGTCGGCACC   1160

AGTTGCGTGAGCGGAAAGATGGCCGCTTCCCGGCCCTGCT   1200

GCAGGGAGCTCAAAATGGAGGACGCGGCGCTCGGGAGAGC   1240

GGGCGGGTGAGTCACCCACACAAAGGAAAAGGGCCTTTCC   1280

GTCCTCAGCCGTCGCTTCATGTGACTCCACGGAGTACCGG   1320

GCGCCGTCCAGGCACCTCGATTAGTTCTCGAGCTTTTGGA   1360

GTACGTCGTCTTTAGGTTGGGGGGAGGGGTTTTATGCGAT   1400

GGAGTTTCCCCACACTGAGTGGGTGGAGACTGAAGTTAGG   1440

CCAGCTTGGCACTTGATGTAATTCTCCTTGGAATTTGCCC   1480

TTTTTGAGTTTGGATCTTGGTTCATTCTCAAGCCTCAGAC   1520

AGTGGTTCAAAGTTTTTTTCTTCCATTTCAGGTGTCGTGA   1560

A.                                         1561                                    (I)
```

2. The essentially pure DNA fragment represented by the following sequence (II):

```
CCCGGGCTGGGCTGAGACCCGCAGAGGAAGACGCTCTAGG    40

GATTTGTCCCGGACTAGCGAGATGGCAAGGCTGAGGACGG    80

GAGGCTGATTGAGAGGCGAAGGTACACCCTAATCTCAATA   120

CAACCTTTGGAGCTAAGCCAGCAATGGTAGAGGGAAGATT   160

CTGCACGTCCCTTCCAGGCGGCCTCCCCGTCACCACCCCC   200

CCCAACCCGCCCCGACCGGAGCTGAGAGTAATTCATACAA   240

AAGGACTCGCCCCTGCCTTGGGGAATCCCAGGGACCGTCG   280

TTAAACTCCCACTAACGTAGAACCCAGAGATCGCTGCGTT   320

CCCGCCCCCTCACCCGCCCGCTCTCGTCATCACTGAGGTG   360

GAGAAGAGCATGCGTGAGGCTCCGGTGCCCGTCAGTGGGC   400

AGAGCGCACATCGCCCACAGTCCCCGAGAAGTTGGGGGGA   440

GGGGTCGGCAATTGAACCGGTGCCTAGAGAAGGTGGCGCG   480

GGGTAAACTGGGAAAGTGATGTCGTGTACTGGCTCCGCCT   520

TTTTCCCGAGGGTGGGGAGAACCGTATATAAGTG.        555                                    (II)
```

3. The essentially pure DNA fragment represented by the following sequence (III):

```
CCCGGGCTGGGCTGAGACCCGCAGAGGAAGACGCTCTAGG    40

GATTTGTCCCGGACTAGCGAGATGGCAAGGCTGAGGACGG    80

GAGGCTGATTGAGAGGCGAAGGTACACCCTAATCTCAATA   120

CAACCTTTGGAGCTAAGCCAGCAATGGTAGAGGGAAGATT   160

CTGCACGTCCCTTCCAGGCGGCCTCCCCGTCACCACCCCC   200
```

```
CCCAACCCGCCCCGACCGGAGCTGAGAGTAATTCATACAA   240
AAGGACTCGCCCCTGCCTTGGGGAATCCCAGGGACCGTCG   280
TTAAACTCCCACTAACGTAGAACCCAGAGATCGCTGCGTT   320
CCCGCCCCCTCACCCGCCCGCTCTCGTCATCACTGAGGTG   360
GAGAAGAGCATGCGTGAGGCTCCGGTGCCCGTCAGTGGGC   400
AGAGCGCACATCGCCCACAGTCCCCGAGAAGTTGGGGGGA   440
GGGGTCGGCAATTGAACCGGTGCCTAGAGAAGGTGGCGCG   480
GGGTAAACTGGGAAAGTGATGTCGTGTACTGGCTCCGCCT   520
TTTTCCCGAGGGTGGGGGAGAACCGTATATAAGTGCAGTA   560
GTCGCCGTGAACGTTCTTTTTCG,   583              (III)
```

4. The essentially pure DNA fragment represented by the following sequence (IV):

```
CCCGGGCTGGGCTGAGACCCGCAGAGGAAGACGCTCTAGG   40
GATTTGTCCCGGACTAGCGAGATGGCAAGGCTGAGGACGG   80
GAGGCTGATTGAGAGGCGAAGGTACACCCTAATCTCAATA   120
CAACCTTTGGAGCTAAGCCAGCAATGGTAGAGGGAAGATT   160
CTGCACGTCCCTTCCAGGCGGCCTCCCCGTCACCACCCCC   200
CCCAACCCGCCCCGACCGGAGCTGAGAGTAATTCATACAA   240
AAGGACTCGCCCCTGCCTTGGGGAATCCCAGGGACCGTCG   280
TTAAACTCCCACTAACGTAGAACCCAGAGATCGCTGCGTT   320
CCCGCCCCCTCACCCGCCCGCTCTCGTCATCACTGAGGTG   360
GAGAAGAGCATGCGTGAGGCTCCGGTGCCCGTCAGTGGGC   400
AGAGCGCACATCGCCCACAGTCCCCGAGAAGTTGGGGGGA   440
GGGGTCGGCAATTGAACCGGTGCCTAGAGAAGGTGGCGCG   480
GGGTAAACTGGGAAAGTGATGTCGTGTACTGGCTCCGCCT   520
TTTTCCCGAGGGTGGGGGAGAACCGTATATAAGTGCAGTA   560
GTCGCCGTGAACGTTCTTTTTCGCAACGGGTTTGCCGCC.  599  (IV)
```

5. An expression plasmid containing the DNA fragment according to claim 1.

6. An expression plasmid according to claim 5, wherein the plasmid is pEF321-CAT.

7. An expression plasmid containing a DNA fragment according to claim 2.

8. An expression plasmid according to claim 7, wherein the plasmid is pEF220-CAT.

9. An expression plasmid containing a DNA fragment according to claim 3.

10. An expression plasmid according to claim 9, wherein the plasmid is pEF223-CAT.

11. An expression plasmid containing a DNA fragment according to claim 4.

12. An expression plasmid according to claim 11, wherein the plasmid is pEF204-CAT.

13. An essentially pure DNA fragment comprising all or a portion of the DNA fragment represented by the following sequence (I):

```
CCCGGGCTGGGCTGAGACCC
                        GCAGAGGAAGACGCTCTAGG   40
GATTTGTCCCGGACTAGCGA
                        GATGGCAAGGCTGAGGACGG   80
GAGGCTGATTGAGAGGCGAA
                        GGTACACCCTAATCTCAATA   120
CAACCTTTGGAGCTAAGCCA
                        GCAATGGTAGAGGGAAGATT   160
CTGCACGTCCCTTCCAGGCG
                        GCCTCCCCGTCACCACCCCC   200
CCCAACCCGCCCCGACCGGA
                        GCTGAGAGTAATTCATACAA   240
AAGGACTCGCCCCTGCCTTG
                        GGGAATCCCAGGGACCGTCG   280
TTAAACTCCCACTAACGTAG
                        AACCCAGAGATCGCTGCGTT   320
```

```
                                    -continued
CCCGCCCCCTCACCCGCCCG
              CTCTCGTCATCACTGAGGTG  360
GAGAAGAGCATGCGTGAGGC
              TCCGGTGCCCGTCAGTGGGC  400
AGAGCGCACATCGCCCACAG
              TCCCCGAGAAGTTGGGGGGA  440
GGGGTCGGCAATTGAACCGG
              TGCCTAGAGAAGGTGGCGCG  480
GGGTAAACTGGGAAAGTGAT
              GTCGTGTACTGGCTCCGCCT  520
TTTTCCCGAGGGTGGGGGAG
              AACCGTATATAAGTGCAGTA  560
GTCGCCGTGAACGTTCTTTT
              TCGCAACGGGTTTGCCGCCA  600
GAACACAGGTAAGTGCCGTG
              TGTGGTTCCCGCGGGCCTGG  640
CCTCTTTACGGGTTATGGCC
              CTTGCGTGCCTTGAATTACT  680
TCCACGCCCCTGGCTGCAGT
              ACGTGATTCTTGATCCCGAG  720
CTTCGGGTTGGAAGTGGGTG
              GGAGAGTTCGAGGCCTTGCG  760
CTTAAGGAGCCCCTTCGCCT
              CGTGCTTGAGTTGAGGCCTG  800
GCCTGGGCGCTGGGGCCGCC
              GCGTGCGAATCTGGTGGCAC  840
CTTCGCGCCTGTCTCGCTGC
              TTTCGATAAGTCTCTAGCCA  880
TTTAAAATTTTGATGACCT
              GCTGCGACGCTTTTTTTCTG  920
GCAAGATAGTCTTGTAAATG
              CGGGCCAAGATCTGCACACT  960
GGTATTTCGGTTTTTGGGGC
              CGCGGGCGGCGACGGGGCCC  1000
```

```
                                    -continued
GTGCGTCCCAGCGCACATGT
              TCGGCGAGGCGGGGCCTGCG  1040
AGCGCGGCCACCGAGAATCG
              GACGGGGGTAGTCTCAAGCT  1080
GGCCGGCCTGCTCTGGTGCC
              TGGCCTCGCGCCGCCGTGTA  1120
TCGCCCCGCCCTGGGCGGCA
              AGGCTGGCCCGGTCGGCACC  1160
AGTTGCGTGAGCGGAAAGAT
              GGCCGCTTCCCGGCCCTGCT  1200
GCAGGGAGCTCAAAATGGAG
              GACGCGGCGCTCGGGAGAGC  1240
GGGCGGGTGAGTCACCCACA
              CAAAGGAAAAGGGCCTTTCC  1280
GTCCTCAGCCGTCGCTTCAT
              GTGACTCCACGGAGTACCGG  1320
GCGCCGTCCAGGCACCTCGA
              TTAGTTCTCGAGCTTTTGGA  1360
GTACGTCGTCTTTAGGTTGG
              GGGGAGGGGTTTTATGCGAT  1400
GGAGTTTCCCCACACTGAGT
              GGGTGGAGACTGAAGTTAGG  1440
CCAGCTTGGCACTTGATGTA
              ATTCTCCTTGGAATTTGCCC  1480
TTTTTGAGTTTGGATCTTGG
              TTCATTCTCAAGCCTCAGAC  1520
AGTGGTTCAAAGTTTTTTTC
              TTCCATTTCAGGTGTCGTGA  1560
A  1561
``` said portion containing the promoter for the human polypeptide chain elongation factor-1α gene which when operably linked to a heterologous structural gene regulates the transcription thereof.

14. An expression plasmid containing the DNA fragment according to claim 13.